US012746376B2

(12) United States Patent
Campbell et al.

(10) Patent No.: US 12,746,376 B2
(45) Date of Patent: Sep. 29, 2026

(54) CONFORMABLE BALLOON DEVICES AND METHODS

(71) Applicant: W. L. Gore & Associates, Inc., Newark, DE (US)

(72) Inventors: Carey V. Campbell, Flagstaff, AZ (US); Matthew E. Maulding, Flagstaff, AZ (US); Benjamin M. Trapp, Phoenix, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 368 days.

(21) Appl. No.: 18/201,255

(22) Filed: May 24, 2023

(65) Prior Publication Data

US 2023/0293862 A1 Sep. 21, 2023

Related U.S. Application Data

(60) Division of application No. 16/843,581, filed on Apr. 8, 2020, now Pat. No. 11,690,984, which is a (Continued)

(51) Int. Cl.

*A61M 25/10* (2013.01)
*A61F 2/958* (2013.01)
*A61F 2/82* (2013.01)

(52) U.S. Cl.

CPC .......... *A61M 25/104* (2013.01); *A61F 2/958* (2013.01); *A61M 25/1002* (2013.01); (Continued)

(58) Field of Classification Search

CPC ............ A61M 25/104; A61M 25/1002; A61M 25/1027; A61M 25/1029; A61M 25/1034; (Continued)

(56) References Cited

U.S. PATENT DOCUMENTS 4,771,776 A 9/1988 Powell et al.
4,941,877 A 7/1990 Montano, Jr.
(Continued)

FOREIGN PATENT DOCUMENTS

CN 1642593 A 7/2005
CN 102488955 A 6/2012
(Continued)

OTHER PUBLICATIONS

Annex to Form PCT/ISA/206 Communication Relating to the Results of the Partial International Search Report and Written Opinion for PCT/US2012/059024 mailed Dec. 17, 2012, corresponding to U.S. Appl. No. 13/645,414.
(Continued)

*Primary Examiner* — Andrew L Swanson

(57) ABSTRACT

The present disclosure is directed toward a semi-compliant to non-compliant, conformable balloon useful in medical applications. Conformable balloons of the present disclosure exhibit a low straightening force when in a curved configuration and at inflation pressures greater than 4 atm. Balloons of the present disclosure are constructed of material that can compress along an inner length when the balloon is in a curved configuration. In further embodiments, balloons of the present disclosure can be constructed of material that sufficiently elongates along an outer arc when the balloon is in a curved configuration. As a result, medical balloons, in accordance with the present disclosure, when inflated in a curved configuration, exhibit kink-free configurations and do not cause a significant degree of vessel straightening.

20 Claims, 20 Drawing Sheets

Related U.S. Application Data continuation of application No. 15/660,316, filed on Jul. 26, 2017, now Pat. No. 10,617,853, which is a continuation of application No. 15/231,494, filed on Aug. 8, 2016, now Pat. No. 10,076,642, which is a continuation of application No. 14/209,711, filed on Mar. 13, 2014, now Pat. No. 9,669,194.

(60) Provisional application No. 61/786,022, filed on Mar. 14, 2013.

(52) U.S. Cl.
CPC .... *A61F 2002/826* (2013.01); *A61M 25/1027* (2013.01); *A61M 25/1029* (2013.01); *A61M 25/1034* (2013.01); *A61M 2025/105* (2013.01); *A61M 2025/1075* (2013.01); *A61M 2025/1084* (2013.01); *A61M 2025/1086* (2013.01); *A61M 2025/1088* (2013.01)

(58) Field of Classification Search
CPC .... A61M 2025/105; A61M 2025/1075; A61M 2025/1084; A61M 2025/1086; A61M 2025/1088; A61F 2/958; A61F 2002/826
See application file for complete search history.

(56) References Cited

U.S. PATENT DOCUMENTS 4,943,275 A 7/1990 Stricker
4,950,232 A 8/1990 Ruzicka et al.
5,236,413 A 8/1993 Feiring
5,250,070 A 10/1993 Parodi
5,334,148 A 8/1994 Martin
5,409,458 A 4/1995 Khairkhahan et al.
5,447,497 A 9/1995 Sogard et al.
5,458,568 A 10/1995 Racchini et al.
5,470,313 A 11/1995 Crocker et al.
5,476,589 A 12/1995 Bacino
5,484,411 A 1/1996 Inderbitzen et al.
5,487,730 A 1/1996 Marcadis et al.
5,545,132 A 8/1996 Fagan et al.
5,620,457 A 4/1997 Pinchasik et al.
5,693,014 A 12/1997 Abele et al.
5,708,044 A 1/1998 Branca
5,746,968 A 5/1998 Radisch, Jr.
5,759,172 A 6/1998 Weber et al.
5,858,990 A 1/1999 Walsh
5,885,259 A 3/1999 Berg
5,913,871 A 6/1999 Werneth et al.
5,954,740 A 9/1999 Ravenscroft et al.
5,954,745 A 9/1999 Gertler et al.
6,007,545 A 12/1999 Venturelli
6,022,359 A 2/2000 Frantzen
6,039,757 A 3/2000 Edwards et al.
6,048,332 A 4/2000 Duffy et al.
6,120,477 A 9/2000 Campbell et al.
6,129,706 A 10/2000 Janacek
6,245,040 B1 6/2001 Inderbitzen et al.
6,261,260 B1 7/2001 Maki et al.
6,478,807 B1 11/2002 Foreman et al.
6,527,739 B1 3/2003 Bigus et al.
6,541,589 B1 4/2003 Baillie
6,676,667 B2 1/2004 Mareiro et al.
6,736,841 B2 5/2004 Musbach et al.
6,814,730 B2 11/2004 Li
6,835,189 B2 12/2004 Musbach et al.
6,841,213 B2 1/2005 Parsonage et al.
6,875,197 B1 4/2005 Simhambhatla et al.
6,942,680 B2 9/2005 Grayzel et al.
6,989,025 B2 1/2006 Burgmeier et al.
6,991,617 B2 1/2006 Hektner et al.
7,004,963 B2 2/2006 Wang et al.
7,008,438 B2 3/2006 O'Brien
7,049,380 B1 5/2006 Chang et al.
7,056,276 B2 6/2006 Nakano et al.
7,083,639 B2 8/2006 Guinan et al.
7,195,638 B1 3/2007 Sridharan
7,273,471 B1 9/2007 Wang et al.
7,303,572 B2 12/2007 Melsheimer et al.
7,306,616 B2 12/2007 Eidenschink et al.
7,335,184 B2 2/2008 Laguna
7,531,611 B2 5/2009 Sabol et al.
7,572,270 B2 8/2009 Johnson
7,686,824 B2 3/2010 Konstantino et al.
7,776,078 B2 8/2010 Burgmeier et al.
7,927,362 B2 4/2011 Shippy et al.
7,976,497 B2 7/2011 Shah et al.
8,048,028 B2 11/2011 Horn et al.
8,048,093 B2 11/2011 Mapes et al.
8,048,440 B2 11/2011 Chang et al.
8,083,761 B2 12/2011 Meens
8,216,267 B2 7/2012 Pallazza
8,221,484 B2 7/2012 Wesselmann
8,292,912 B2 10/2012 Burton et al.
8,637,144 B2 1/2014 Ford
9,139,669 B2 9/2015 Xu et al.
9,149,612 B2 10/2015 Chuter
9,669,194 B2 6/2017 Campbell et al.
10,076,642 B2 9/2018 Campbell et al.
11,690,984 B2 7/2023 Campbell et al.
2001/0035456 A1 11/2001 Lennox
2002/0045914 A1 4/2002 Roberts et al.
2002/0161388 A1 10/2002 Samuels et al.
2003/0032999 A1 2/2003 Huang
2003/0153870 A1 8/2003 Meyer et al.
2003/0163154 A1 8/2003 Miyata et al.
2004/0122508 A1 6/2004 White et al.
2004/0236398 A1 11/2004 Burgmeier et al.
2005/0137621 A1 6/2005 Stahl et al.
2005/0149082 A1 7/2005 Yee et al.
2005/0177130 A1 8/2005 Konstantino et al.
2005/0216047 A1 9/2005 Kumoyama et al.
2006/0136032 A1* 6/2006 Legarda ............ A61M 25/1006 623/1.11
2006/0178685 A1 8/2006 Melsheimer
2007/0061006 A1 3/2007 Desatnik et al.
2007/0088323 A1 4/2007 Campbell et al.
2007/0106216 A1 5/2007 Noddin
2007/0289117 A1* 12/2007 Huang .................... A61F 2/958 29/508
2008/0065188 A1 3/2008 Pallazza
2008/0097301 A1 4/2008 Alpini et al.
2008/0147103 A1 6/2008 Shekalim
2008/0294103 A1 11/2008 Pereira
2009/0124969 A1 5/2009 Lenz
2009/0182413 A1* 7/2009 Burkart ..................... A61F 2/07 623/1.16
2009/0226502 A1 9/2009 Chen
2009/0281490 A1 11/2009 Mcauley et al.
2009/0281564 A1 11/2009 Kontos
2009/0283206 A1 11/2009 Eskaros et al.
2009/0299450 A1 12/2009 Johnson et al.
2009/0306700 A1 12/2009 Miyata et al.
2009/0326574 A1 12/2009 Kilpatrick et al.
2010/0036314 A1 2/2010 Burton et al.
2010/0042198 A1 2/2010 Burton
2010/0094209 A1 4/2010 Drasler et al.
2010/0189876 A1 7/2010 Kokish et al.
2010/0312182 A1 12/2010 Adden et al.
2011/0046711 A1 2/2011 Degen et al.
2011/0152683 A1 6/2011 Gerrans et al.
2011/0172598 A1 7/2011 Sampognaro et al.
2011/0230946 A1 9/2011 Butcher et al.
2012/0059401 A1* 3/2012 Konstantino ........... A61F 2/958 606/159
2012/0083733 A1 4/2012 Chappa
2014/0276406 A1 9/2014 Campbell et al.
2015/0081006 A1 3/2015 Chuter et al.
2015/0133988 A1 5/2015 Chuter
2015/0209556 A1 7/2015 Timothy
2016/0339215 A1 11/2016 Campbell et al.

(56) References Cited

U.S. PATENT DOCUMENTS

| | | | |
|---|---|---|---|
| 2017/0319829 | A1 | 11/2017 | Campbell et al. |
| 2020/0230377 | A1 | 7/2020 | Campbell et al. |

FOREIGN PATENT DOCUMENTS

| | | | |
|---|---|---|---|
| DE | 19952505 | A1 | 5/2001 |
| EP | 0745395 | A2 | 12/1996 |
| EP | 0808613 | A1 | 11/1997 |
| EP | 0872253 | A2 | 10/1998 |
| EP | 1338300 | A1 | 8/2003 |
| EP | 1604704 | A1 | 12/2005 |
| EP | 1683541 | A2 | 7/2006 |
| EP | 1892007 | A1 | 2/2008 |
| EP | 2431067 | A1 | 3/2012 |
| GB | 1327858 | A | 8/1973 |
| JP | 02-174849 | A | 7/1990 |
| JP | 08-052219 | A | 2/1996 |
| JP | 09-506805 | A | 7/1997 |
| JP | 10-118195 | A | 5/1998 |
| JP | 11-319103 | A | 11/1999 |
| JP | 2001-515772 | A | 9/2001 |
| JP | 2002-045435 | A | 2/2002 |
| JP | 2003-320031 | A | 11/2003 |
| JP | 2005-349202 | A | 12/2005 |
| JP | 2007-502687 | A | 2/2007 |
| JP | 2007-526089 | A | 9/2007 |
| JP | 2009-540928 | A | 11/2009 |
| JP | 2011-513005 | A | 4/2011 |
| WO | 87/01600 | A1 | 3/1987 |
| WO | 97/10871 | A1 | 3/1997 |
| WO | 97/17889 | A1 | 5/1997 |
| WO | 01/45781 | A1 | 6/2001 |
| WO | 02/22198 | A2 | 3/2002 |
| WO | 2007/095705 | A1 | 8/2007 |
| WO | 2007/149464 | A2 | 12/2007 |
| WO | 2008/021003 | A1 | 2/2008 |
| WO | 2009/111716 | A1 | 9/2009 |
| WO | 2011/112863 | A1 | 9/2011 |
| WO | 2012/142540 | A1 | 10/2012 |
| WO | 2013/009740 | A1 | 1/2013 |

OTHER PUBLICATIONS

Fiss, David. "Normal Coronary Anatomy and Anatomic Variations". Jan. 18, 2007. Applied Radiology, The Jounral of Practical Medical Imaging and Management.

Grip.TM. by Acrostak—Product Specification Sheet and Brochure.

Gurbel PA, Anderson RD, Peels HO, van Boven AJ, den Heijer P. Coronary Artery Angioplasty with a Helical Autoperfusion Balloon Catheter. Catheterization and Cardiovascular Diagnosis (Online) Feb. 1997, 40(2); 179-185. (Abstract).

Hosokawa et al., Successful Treatment for Refractory Coronary Thrombus with Scoring Saloon Angioplasty, Catheterization and Cardiovascular Interventions, vol. 79, No. 2, Feb. 1, 2012, pp. 282-287.

Hosokawa Y, Tanaka K, Mizuno K. Successful Treatment for Refractory Coronary Thrombus with Scoring Balloon Angioplasty. Catheterization and Cardiovascular Interventions (Online) 2012, 79:282-287.

International Preliminary Report on Patentability received for PCT Patent Application No. PCT/US2014/027615, mailed on Sep. 24, 2015, 14 pages.

International Search Report and Written Opinion for PCT/US2012/059024 dated Feb. 6, 2013, corresponding to U.S. Appl. No. 13/645,414.

International Search Report and Written Opinion for PCT/US2012/059024 mailed Feb. 6, 2013, corresponding to U.S. Appl. No. 13/645,414.

International Search Report and Written Opinion for PCT/US2014/027615 dated Sep. 15, 2014, corresponding to U.S. Appl. No. 14/209,711; 7 pages.

Japanese Application No. 2014-534792, Office Action mailed on Sep. 6, 2016, 37 pages (24 pages of English Translation and 13 pages of Original document).

Niazmand et al. "Bend Sweep Angle and Reynolds Number Effects on Hemodynamics of S-Shaped Arteries". Apr. 29, 2010. Annals of Biomedical Engineering. vol. 38, Iss. 9, p. 2817-2828.

Office Action, Japanese Patent Application 2014-534792, Aug. 30, 2016, 37 pages.

Prosi et al. "Influence of curvature dynamics on pulsatile coronary artery flow in a realistic bifurcation model". Apr. 27, 2004. Journal of Biomechanics. vol. 37, Iss. 11, Nov. 2004. p. 1767-1775.

* cited by examiner

| | | Circumferential | | Longitudinal | | | | |
|---|---|---|---|---|---|---|---|---|
| Balloon | Sample | Stiffness (gf/mm/mm) | Mean Circ Stifness (gf/mm/mm) | Max Load (kgf) | Stiffness (gf/mm/mm) | Mean Long Stiffness (gf/mm/mm) | Stiffness Balance Ratio (af/mm/mm) | Mean Long Load at Elongation (kgf) |
| Creagh | 1 | 457.8 | 429.7 | 2.68 | 320.2 | 374.5 | 1.1 | 2.98 |
| | 2 | 450.3 | | 3.12 | 394.5 | | | |
| | 3 | 363.1 | | 3.15 | 408.8 | | | |
| Fox | 1 | 248.0 | 241.4 | 2.59 | 218.0 | 199.0 | 1.2 | 2.23 |
| | 2 | 253.6 | | 1.71 | 181.8 | | | |
| | 3 | 222.6 | | 2.39 | 197.0 | | | |
| Workhorse | 1 | 853.9 | 1002.4 | 1.11 | 514.1 | 536.8 | 1.9 | 1.27 |
| | 2 | 1067.0 | | 1.07 | 498.6 | | | |
| | 3 | 1086.2 | | 1.64 | 597.8 | | | |
| Hi TD MTS | 1 | 351.8 | 380.1 | 0.46 | 28.5 | 23.4 | 16.2 | 0.38 |
| | 2 | 409.8 | | 0.35 | 21.5 | | | |
| | 3 | 378.6 | | 0.32 | 20.4 | | | |
| Med TD MTS | 1 | 437.8 | 425.1 | 0.22 | 13.4 | 17.5 | 24.3 | 0.30 |
| | 2 | 383.2 | | 0.37 | 21.1 | | | |
| | 3 | 454.3 | | 0.32 | 18.0 | | | |
| Lo TD MTS | 1 | 270.9 | 329.6 | 0.15 | 6.7 | 9.9 | 33.4 | 0.18 |
| | 2 | 285.8 | | 0.19 | 9.8 | | | |
| | 3 | 431.9 | | 0.21 | 13.2 | | | |

FIG. 8

Straightening Force (N) at Pressure

| Sample | 5 atm | 6 atm | 7 atm | 8 atm | 9 atm | 10 atm | 12 atm | 13 atm | 15 atm | 16 atm | 17 atm | 25 atm |
|---|---|---|---|---|---|---|---|---|---|---|---|---|
| Conq 8mm | — | 15.01 | — | 18.24 | — | — | — | — | — | 31.75 | — | 45.04 |
| Work 8mm | — | 14.46 | — | — | — | 19.11 | 20.94 | — | — | 22.87 | — | — |
| Fox 3mm | — | 1.91 | — | — | — | 2.27 | — | 2.8 | — | — | 3.36 | — |
| Fox 5mm | — | — | — | — | 5 | — | — | 6.5 | — | — | 7.8 | — |
| Fox 8mm | — | 6.49 | — | — | 9.42 | — | 12.73 | — | 15.98 | — | — | — |
| Fox 12mm | 9.7 | 12.5 | 15.4 | 18.7 | — | — | — | — | — | — | — | — |
| Ex 7-3mm | — | 1.85 | — | — | — | 2.24 | — | 2.44 | — | — | 2.58 | — |
| Ex 8-5mm | — | 2.2 | — | — | 2.7 | — | — | 2.8 | — | — | 3.2 | — |
| Ex 9-8mm | — | 4 | — | — | — | — | 4.9 | — | — | 3.88 | — | — |
| Ex 10-12mm | 5.1 | 6.2 | 7.5 | 7.8 | — | — | — | — | — | — | — | — |

FIG. 12

CONFORMABLE BALLOON DEVICES AND METHODS

CROSS-REFERENCE TO RELATED APPLICATION

This application is a divisional application of U.S. application Ser. No. 16/843,581, filed Apr. 8, 2020, which is a continuation application of U.S. application Ser. No. 15/660,316 filed on Jul. 26, 2017, now U.S. Pat. No. 10,617,853, issued on Apr. 14, 2020, which is a continuation application of U.S. application Ser. No. 15/231,494 filed on Aug. 8, 2016, now U.S. Pat. No. 10,076,642, issued on Sep. 18, 2018, which is a continuation application of U.S. application Ser. No. 14/209,711 filed on Mar. 13, 2014, now U.S. Pat. No. 9,669,194, issued on Jun. 6, 2017, which claims priority to U.S. Provisional Application No. 61/786,022, filed on Mar. 14, 2013 and entitled "CONFORMABLE BALLOON DEVICES AND METHODS", wherein the above-listed applications are hereby incorporated by reference in their entireties.

FIELD

The present disclosure generally relates to medical balloons, and more particularly semi-compliant to non-compliant medical balloons that are conformable to a curved vessel.

BACKGROUND

There are two main types of mechanical stresses present during a typical inflation of an elongated balloon. Hydraulic loading on a generally cylindrical balloon wall results in hoop stress and longitudinal stress. The result of the inflation loading depends on the type of material from which the balloon walls are constructed. In simplified terms, for a compliant balloon, the load will result in the balloon adapting to the shape of surrounding constraints. For example, in a body vessel, the balloon will inflate up to contact with the vessel wall(s) and then continue to lengthen down the length of the vessel as more inflation medium is introduced into the balloon. For non-compliant balloons, the shape is defined by the configuration of the balloon walls as manufactured rather than surrounding constraints, and as inflation medium is introduced, the pressure increases while the volume remains relatively constant. When a generally cylindrical non-compliant balloon is inflated in a curved vessel, the tendency is to maintain the molded balloon shape, usually a straight shape, and thus stress the vessel walls.

Percutaneous transluminal angioplasty (PTA) balloons, which are semi-compliant to non-compliant balloons, are designed to operate at pressures between 5 to 30 atmospheres ("atm") and do not readily conform to a curved configuration, in particular tortuous anatomies, e.g., curved body vessels. More precisely, medical angioplasty balloons when inflated in a curved configuration tend toward a straight configuration as the balloon is inflated to angioplasty pressures. This tendency to straighten is characterized herein in terms of a straightening force. As one might expect, such balloons, when extended along the vessel curvature, are impeded from straightening by the surrounding vessel. As a result, the balloon can cause unwanted straightening of, and damage to, the vessel, and/or the angioplasty balloon can kink. These balloons do not typically conform to the surrounding constraints, particularly when the surrounding constraints involve certain amounts of curvature.

Medical balloons capable of operating at angioplasty pressures yet having a low or insignificant straightening force when in a curved configuration can be useful in many applications.

SUMMARY

In accordance with one aspect of the disclosure, a medical balloon can comprise a balloon wall material defining a chamber wherein a portion of the balloon wall along an inner arc undergoes at least 5% compressive strain when inflated in a curved configuration requiring 20% strain; wherein said medical balloon is semi-compliant to non-compliant.

In accordance with another aspect of the disclosure, a medical balloon having a length along a longitudinal axis can comprise a balloon wall material having a porous microstructure, wherein the balloon wall material comprises a circumferential stiffness and a longitudinal stiffness and wherein the circumferential stiffness is at least 5 times greater than the longitudinal stiffness. In various embodiments, the circumferential stiffness can be at least 8 times greater, 10 times greater, 15 times greater, 25 times greater, or 50 times greater than the longitudinal stiffness.

In accordance with another aspect of the disclosure, a method of making a medical balloon can comprise wrapping an anisotropic, porous film about a mandrel having a diameter slightly greater than a nominal diameter at an angle greater than 75 degrees with respect to a longitudinal axis to form a tubular precursor, wherein the tubular precursor has a longitudinal stiffness that is at least 5 times less than a circumferential stiffness; and securing the tubular precursor about a compliant bladder to form a balloon cover. During manufacture, the medical balloon may be inflated to the nominal diameter and then radially compacted to a delivery profile, wherein, upon radial compaction, the balloon cover forms a plurality of randomly oriented folds that are much shorter than the length of the balloon, e.g., less than 20% of the balloon length.

In accordance with another aspect of the disclosure, a medical balloon can comprise a balloon comprising a polymeric material and having a nominal diameter between 3 mm to 8 mm and a nominal inflation pressure at or below 10 atm, where the balloon exhibits less than a 25% increase in mean straightening force when inflated from a pressure of 10 atm to 16 atm while in a curved conformation requiring 16% total strain. In addition, other diameter balloons are also contemplated. For example, a medical balloon can comprise a balloon comprising a semi-compliant to non-compliant balloon comprising a polymeric material and having a nominal diameter between 9 mm to 12 mm and a nominal pressure at or below 6 atm, where the balloon exhibits less than a 3N increase in mean straightening force when inflated from a pressure of 5 atm to 8 atm while in a curved conformation requiring 16% total strain. In some examples, the balloon exhibits less than a 3N increase mean straightening force when inflated across the working pressure range and the medical balloon exhibits less than a 10N mean straightening force when inflated at the rated burst pressure while in a curved configuration requiring 16% total strain. Also, a medical balloon can comprise a balloon comprising a polymeric material and having a nominal diameter between 13 mm to 14 mm and a nominal inflation pressure at or below 6 atm, where the balloon exhibits less than a 4N increase in mean straightening force when inflated from a pressure of 6 atm to 8 atm while in a curved conformation requiring 16% total strain. In some examples, the medical balloon may exhibit less than a 12N mean straightening force when inflated across the working pressure range while in a curved configuration requiring 16% total strain. In accordance with another aspect of the disclosure, a medical balloon can comprise a balloon comprising a polymeric material and having a nominal diameter between 3 mm to 8 mm and a working pressure range that spans a nominal inflation pressure to a rated burst pressure, where the balloon exhibits less than a 25% increase in mean straightening force when inflated across the working pressure range while in a curved conformation requiring 16% total strain, and where the nominal inflation pressure is at least 4 atm. In addition, other diameter balloons are also contemplated. For example, a medical balloon can comprise a balloon comprising a polymeric material and having a nominal diameter between about 9 mm to about 12 mm and a working pressure range that spans a nominal inflation pressure to a rated burst pressure, where the balloon exhibits less than a 3N increase in mean straightening force when inflated across the working pressure range while in a curved conformation requiring 16% total strain, and where the nominal inflation pressure is at least 4 atm. Also, a medical balloon can comprise a balloon comprising a polymeric material, and having a nominal diameter having the nominal diameter between about 13 mm to about 14 mm and a working pressure range spans a nominal inflation pressure to a rated burst pressure, where the balloon exhibits less than a 5N increase in mean straightening force when inflated across the working pressure range while in a curved conformation requiring 16% total strain, and where the nominal inflation pressure is at least 4 atm.

In accordance with another aspect of the disclosure, a medical balloon can comprise a balloon comprising a polymeric material and being inflatable to a rated burst pressure, the balloon having a nominal diameter of 3 mm to 12 mm where at the rated burst pressure, the balloon exhibits a straightening force as a function of balloon diameter (d) of less than 0.86(Diameter)+0.20 when in a curved conformation requiring 16% total strain, where the rated burst pressure is at least 4 atm.

In accordance with another aspect of the disclosure, a medical balloon can comprise a balloon comprising a polymeric material that can become plastically deformed upon inflation of the balloon to a pressure within the working pressure range such that when inflated in a curved configuration having a bend radius and requiring 16% strain, the balloon upon re-inflation, without any surrounding constraints and to a pressure within the working pressure range, comprises a curved configuration having a bend radius that is less than 200% larger than the initial bend radius. Said balloon is semi-compliant to compliant.

The various aspects of the present disclosure can comprise a variety of additional or alternative features in any combination. In various embodiments, the balloon wall material can remain kink-free when inflated in said curved configuration. Said medical balloon can be semi-compliant to non-compliant. The balloon wall material can comprise a porous microstructure, such as one comprising a node and fibril microstructure and/or be fibrillated. The porous microstructure can be expanded polytetrafluoroethylene. In various embodiments, a portion of the balloon wall material along an inner arc undergoes at least 5% compressive strain when inflated in a curved configuration requiring 20% total strain. In various embodiments, the curved configuration can be such that the portion of the balloon wall material along the inner arc undergoes compressive strain that is at least 30% of the total strain. Similarly, in various embodiments, the curved configuration can require 25% total strain and the portion of the balloon wall material along the inner arc undergoes at least 10% compressive strain. In various embodiments, the working length of the balloon lengthens less than 10% during inflation to at least an angioplasty pressure. In various embodiments, the balloon wall material can remain kink-free when the ratio of a balloon diameter within a working length to a bend radius is at least 1:3. In various embodiments, the medical balloon can further comprise a compliant bladder, such as an elastomeric bladder. The nominal inflation pressures of the conformable balloon in a curved configuration can be greater than 4 atm, greater than 8 atm, greater than 12 atm, greater than 16 atm, greater than 20 atm, or more and remain kink-free. In various embodiments, the balloon wall material comprises a circumferential stiffness greater than 200 gf/mm/mm. In various embodiments, the balloon wall material comprises a circumferential stiffness and a longitudinal stiffness and wherein the circumferential stiffness is at least 5 times greater than the longitudinal stiffness. For example, the longitudinal stiffness can be less than 30 gf/mm/mm for a medical balloon having a 4 mm diameter. In various embodiments, the microstructure of the balloon wall material can be oriented at an angle greater than 80 degrees relative to the longitudinal axis when inflated to the nominal diameter. In various embodiments, the balloon wall material can comprise a membrane wherein the membrane has a balance ratio of at least 10:1. In various embodiments, the balloon wall material can be adapted to perfuse. In various embodiments, the balloon can form varied surface by way of a template having at least one aperture and overlying at least a portion of the balloon wherein the balloon wall material protrudes through the aperture in an inflated configuration. In various embodiments, the outer surface of the medical balloon can be coated with a therapeutic agent and/or utilized for the deployment or touching up of an endoprosthetic device. For example, in various embodiments, the medical balloon can comprise a stent or stent graft disposed about the balloon in a delivery configuration.

BRIEF DESCRIPTION OF THE DRAWINGS

The features and advantages of the present disclosure will become more apparent from the detailed description set forth below when taken in conjunction with the drawings, wherein:

FIG. 8 is a table of data showing balance ratios of the balloon wall materials of both commercially-available PTA balloon devices and various balloon embodiments in accordance with the present disclosure as described in Example 5.

FIG. 12 is a table of data showing the straightening force measurements taken of various balloons in a 3-point bend fixture as described in Example 11.

DETAILED DESCRIPTION OF THE ILLUSTRATED EMBODIMENTS

Figure 1A:
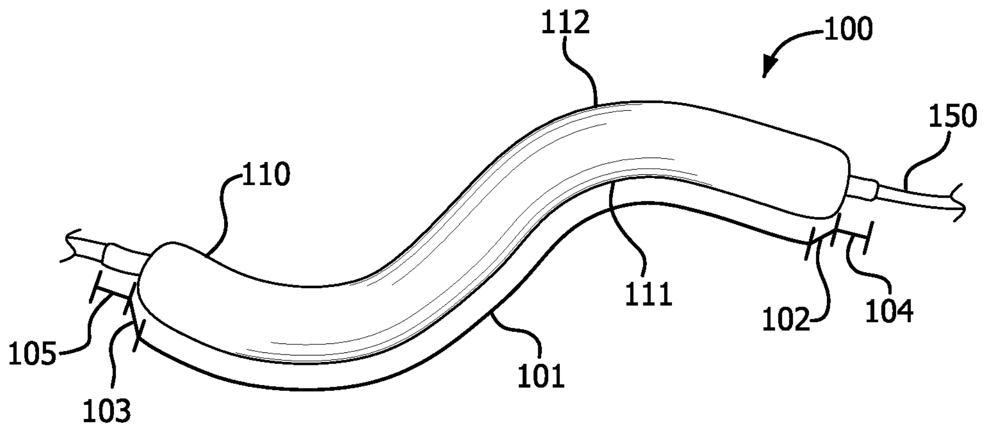
FIG. 1*a* illustrates a medical balloon embodiment in accordance with a present disclosure, inflated in a curved configuration.

Persons skilled in the art will readily appreciate that various aspects of the present disclosure can be realized by any number of methods and apparatuses configured to perform the intended functions. Stated differently, other methods and apparatuses can be incorporated herein to perform the intended functions. It should also be noted that the accompanying drawing figures referred to herein are not all drawn to scale, but may be exaggerated to illustrate various aspects of the present disclosure, and in that regard, the drawing figures should not be construed as limiting. Finally, although the present disclosure may be described in connection with various principles and beliefs, the present disclosure should not be bound by theory.

As used herein, "straightening force" means the amount of force exerted by the balloon on to a constraint as the balloon attempts to return to a straight state. One technique for measuring the amount of straightening force is set forth in Example 11, where the constraint is a 3-point bend fixture.

As used herein, "strain" means the deformation of a material caused by applying an external force to it.

As used herein, "compressive strain" means an amount of material deformation caused by applying a compressive force to a material, i.e., negative strain. Compressive strain can be understood as in-plane compression as distinguished from macro buckling or folding of a material.

As used herein, "tensile strain" means an amount of material deformation caused by applying a tensile force to a material.

As used herein, "nominal diameter" means the approximate diameter of the balloon at the nominal inflation pressure. Beyond this state, pressure increases (e.g., up to the rated burst pressure) result in less than a 20% increase in diameter, less than a 15% increase in diameter, or less than a 10% increase in diameter.

As used herein, "angioplasty pressure" means the minimum pressure required to perform a PTA procedure for a balloon of a certain size. This value is dependent on the size of the balloon, and can be within the working pressure range between the nominal inflation pressure to the rated burst pressure, the nominal inflation pressure being the minimum pressure at which the balloon reaches nominal diameter and rated burst pressure being the upper limit of a pressure range for a medical balloon provided by the manufacturer.

As used herein, "balance ratio" means ratio of machine direction matrix tensile strength to transverse direction matrix tensile strength. Where the matrix tensile strengths in the machine and transverse direction are not substantially equal, a material can be said to be "anisotropic."

As used herein, "stiffness" is a measure of the change in load over an increase or decrease in tested length. Stiffness differs from modulus as it is not normalized for cross sectional area or for gauge length. Modulus is change in stress over change in strain.

As used herein, a "semi-compliant to non-compliant" balloon is one that has less than about 20% diametric growth (e.g., less than a 20% increase in the balloon diameter relative to the nominal diameter) when inflated from the nominal inflation pressure to the rated burst pressure. Balloons of the present disclosure are semi-compliant to non-compliant, and after reaching the nominal inflation pressure, can exhibit less 20% diametric growth, less than 15% diametric growth, or less than 10% diametric growth.

As used herein, "medical device" means any medical device capable of being implanted and/or deployed within a body lumen or cavity. In various embodiments, a medical device can comprise an endovascular medical device such as a stent, a stent-graft, graft, heart valve, heart valve frame or pre-stent, occluder, sensor, marker, closure device, filter, embolic protection device, anchor, drug delivery device, cardiac or neurostimulation lead, gastrointestinal sleeves, and the like.

As used herein, "kink" means a fold, pleat, wrinkle, or similar deformed condition.

As used herein, "mean straightening force" means the mean force measured over the time span that the balloon was held at a specific pressure.

Lastly, the preposition "between," when used to define a range of values (e.g., between x and y) means that the range includes the end points (e.g., x and y) of the given range and the values between the end points.

The present disclosure is directed towards a semi-compliant to non-compliant, conformable balloon useful for medical applications. Conformable balloons of the present disclosure exhibit a low or insignificant straightening force when in a curved configuration and at inflation pressures greater than 4 atm. Balloons of the present disclosure are constructed of material(s) that can compress along an inner arc length when the balloon is in a curved configuration. In further embodiments, balloons of the present disclosure can be constructed of material that sufficiently elongates along an outer arc length when the balloon is in a curved configuration. As a result, medical balloons, in accordance with the present disclosure, can conform to the surrounding curved anatomy. When inflated in a curved configuration, these conformable medical balloons exhibit kink-free inflation and do not cause a significant degree of straightening of body anatomies or "tortuous paths" (e.g., blood vessels), if any at all, at inflation pressures greater than 4 atm.

In addition, the balloon embodiments of the present disclosure can provide substantially uniform vessel contact ("apposition") along their working lengths or intermediate sections. By contrast, if a kink occurs, there will not be uniform vessel contact along the working length. The described embodiments can also provide generally uniform pressure along their working lengths to the entire circumference of a curved anatomy. By contrast, if a kink occurs, there will not be uniform pressure along the working length. Uniform contact and uniform pressures on a curved vessel, for example, can facilitate a more efficient delivery of a therapeutic agent for such embodiments coated with a therapeutic agent. Similarly, uniform contact and uniform pressures on a curved vessel, for example, can facilitate improved device deployment for such embodiments having a deployable device mounted thereon.

The balloon embodiments of the present disclosure can comprise a fluid-tight, compliant bladder so that the balloon does not perfuse. Alternatively, described embodiments can be bladderless and constructed to perfuse at a desired threshold pressure or diameter.

The balloon embodiments of the present disclosure can be part of a balloon assembly adapted to form a protruding topography on the balloon surface. A template having at least one aperture can be located about an underlying conformable balloon. The template is constructed not to circumferentially or longitudinally distend to the same extent as the underlying balloon, thus, at least one surface protrusion would form. Said constructs can be fluid tight or configured to perfuse as well.

Figure 1B:
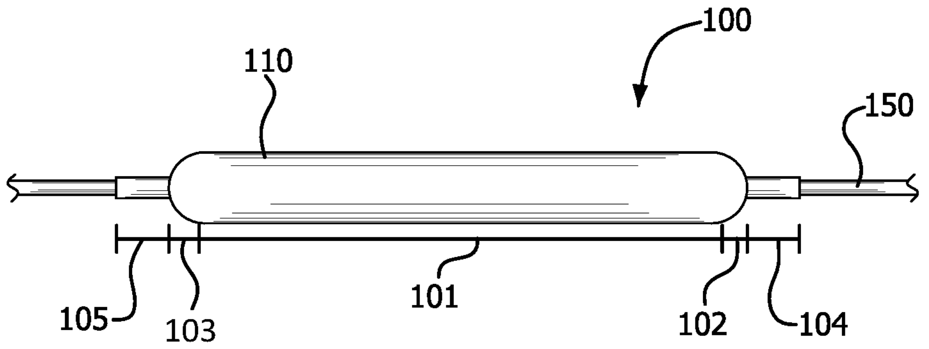
FIG. 1*b* illustrates a medical balloon embodiment in accordance with a present disclosure, inflated in a straight configuration.
Figure 1C:
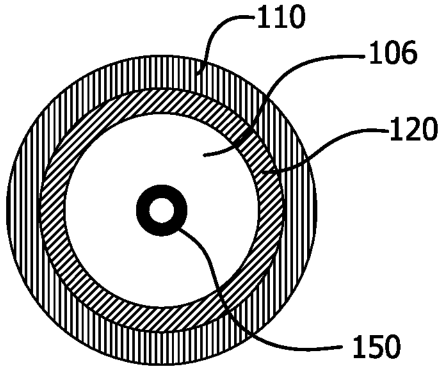
FIG. 1*c* illustrates a schematic view of the cross-section of a medical balloon embodiment in accordance with a present disclosure.

According to the present disclosure, with reference to FIGS. 1*a*-1*c*, a medical balloon 100 comprises a balloon wall 110 defining a chamber 106 wherein a portion of the balloon wall 110 along an inner arc 111 undergoes at least 5% compressive strain when inflated in a curved configuration that requires 20% total strain. As the balloon 100 can be semi-compliant to non-compliant, it is capable of inflation pressures within the range of at least about 4 atm to about 30 atm or more and has less than about 20% diametric growth from the nominal inflation pressure to the rated burst pressure. For example, a working pressure range can be between about 5 atm to about 9 atm, about 9 atm to about 20 atm, or any range within either of these ranges. The medical balloon 100 remains kink-free when inflated to an angioplasty pressure in the specified curved configuration. The balloon 100 of the present disclosure when inflated to at least the angioplasty pressure is capable of retaining a kink-free at curved configuration requiring total strain amounts higher than 20%.

The range of curvature wherein a kink-free inflation can be maintained depends on the dimension of the balloon. In various embodiments, the medical balloon can have a kink-free, curved configuration such that the bend radius is at least three times greater than the balloon diameter as measured within a working length of the balloon 100, e.g., the nominal diameter. In various embodiments, the medical balloon 100 can have a curved configuration such that the ratio of bend radius to balloon diameter is about 2:1; about 3:1; about 4:1; about 5:1; about 6:1; about 7:1; about 8:1; about 9:1; about 10:1; about 11:1; about 12:1; about 13:1; or about 14:1 or more.

The balloon wall 110 comprises a material layer that is compressible, elongatable, or a combination of the two, along the length of the balloon 100. Stated differently, the balloon wall 110 can undergo compressive strain along the portion of the wall 110 defining the inner arc 111 and/or tensile strain along the portion of the balloon wall defining the outer arc 112 when inflated in a curved configuration. In various embodiments, the relative amount of compressive strain can be between about 25% to about 100% of the total strain. Accordingly, when inflated in a curved configuration, the balloon wall 110 can adapt to the changes in length along the portion of the working length of the balloon defining an inner arc 111 and outer arc 112.

In various embodiments, the balloon wall 110 is capable of undergoing at least 5% compressive strain or at least 10% compressive strain, e.g., along the section or sections of the balloon wall 110 that extend along the inner arc 111 of the balloon in a curved conformation. For example, the balloon wall 110 comprises a porous material that facilitates compressive strain along a lengthwise section. Such section of balloon wall 110 can be at least a 5 mm lengthwise section extending along inner arc 111, such as the 1 cm lengthwise section measured in Example 3 to determine compressive strain. While not wishing to be bound by a particular theory, it is believed that compression is facilitated by the void spaces of the porous material that allow for the material bulk to compress and thus reduce the volume of the void spaces.

In various embodiments, a porous material can comprise an expanded polymeric film. In addition, the pores of at least a portion of the porous material can be devoid of any material that can impede compression; e.g., the porous material comprises a plurality of compressible voids. For example, the porous material can comprise a node and fibril microstructure that is free of any imbibed material. In addition, the architecture of porous microstructure can be substantially fibrillated (e.g., a non-woven web having a microstructure of substantially only fibrils, some fused at crossover points or with smaller nodal dimensions). Large nodes or large densified regions may have an impact on the extent of compressibility or compressive stiffness.

In various embodiments, the porous material comprises expanded polytetrafluoroethylene (ePTFE), expanded polyethylene, woven and non-woven fabrics or films, and the like. Non-limiting examples of expandable fluoropolymers include, but are not limited to, expanded PTFE, expanded modified PTFE, and expanded copolymers of PTFE. Patents have been filed on expandable blends of PTFE, expandable modified PTFE, and expanded copolymers of PTFE, such as, for example, U.S. Pat. No. 5,708,044 to Branca; U.S. Pat. No. 6,541,589 to Baillie; U.S. Pat. No. 7,531,611 to Sabol et al.; U.S. patent application Ser. No. 11/906,877 to Ford; and U.S. patent application Ser. No. 12/410,050 to Xu et al.

While in some embodiments the porous material is free of any imbibed materials, in various other embodiments, the porous material can comprise light imbibing and/or sectional imbibing that facilitates balloon compaction or retraction upon deflation but does not significantly impact the ability to undergo compressive strain and/or tensile strain. Such imbibed materials can comprise an elastomer, such as a polyurethane (such as an aromatic polyurethane like Techothane), a thermoplastic fluoroelastomer copolymer of tetrafluoroethylene/perfluoromethylvinylether (TFE/PMVE) as taught in U.S. Pat. Nos. 7,049,380 and 8,048,440, both to Chang et al., silicone, FKM designated fluoroelastomers according to ASTM D1418 (e.g., Viton by DuPont), and/or silicone rubbers. The weight ratio of porous material to imbibed elastomer in the balloon wall 110 can be at least 1:3, 1:2, 2:3, 1:1, 3:2, 2:1, 3:1, 4:1, 5:1 6:1, 7:1, 8:1, 9:1, 10:1, 15:1, 18:1, 19:1, 20:1, or any ratio or range therebetween. In some embodiments, the weight ratio of porous material to imbibed elastomer can be between 2:3 and 3:2. In various embodiments, the balloon wall 110 can be formed from wrapped layers wherein a certain percentage of layers comprise an imbibed porous material. For example, the balloon wall 110 can comprise wrapped layers of porous material, wherein up to 50%, up to 30%, up to 20%, up to 15%, up to 10%, up to 5%, or up to 2% of the wrapped layers are imbibed with an elastomer. In some embodiments, 5% to 30% of the wrapped layers are imbibed with an elastomer. Alternatively or in addition thereto, in various embodiments, a discrete circumferential section of the porous material of balloon wall 110 can be imbibed with an elastomer.

In different or the same embodiments, the material layer can be anisotropic, oriented such that the balloon wall is weaker in the longitudinal direction than the radial direction. The longitudinal stiffness is sufficiently low to provide for some elongation (tensile strain) on the outer arc 112. The preferred amount of longitudinal stiffness can vary with the dimensions (width and length) of the balloon. For example, an 8 mm diameter balloon can have a longitudinal stiffness less than 70 gf/mm/mm, or a 4 mm diameter balloon can have a longitudinal stiffness less than 30 gf/mm/mm. In general, the longitudinal stiffness (also referred to herein as "tensile stiffness") of the anisotropic layer will be sufficiently low so that the balloon does not significantly reorient toward a straight configuration when inflated in a curved configuration at angioplasty pressures greater than 4 atm or more.

While a low longitudinal stiffness facilitates tensile strain along the outer arc 112, in various embodiments, there can be a lower limit to the amount of longitudinal stiffness. Again, the lower limit can depend on the dimensions of the balloon 100. Tensile strain along the outer arc 112 can result in the working length 101 of the balloon 100 lengthening to some degree. While reduced longitudinal stiffness in the balloon wall 110 can contribute to a lower straightening force, being too low can result in excessive lengthening. Excessive lengthening can in many applications be undesirable, and the extent of lengthening should be controlled for a desired pressure. By appropriately selecting the longitudinal stiffness, the working length 101 of the balloon 100, in accordance with the present disclosure, can lengthen less than 10% during inflation to an angioplasty pressure.

In addition, in various embodiments, the balloon wall 110 can more readily compress along the inner arc 111 than distend along the outer arc 112. In other words, the material layer can comprise a compressive stiffness less than the tensile stiffness.

The total strain can be calculated by the method described in Example 4. By way of example, an 8 mm balloon in a 32 mm bend radius requires about 11% to 25% total strain to have a low or insignificant straightening force and/or remain kink-free. The precise value is dependent on the manner in which material layer responds to being stressed when in a curved conformation. A material layer can exhibit equal amounts of compressive and tensile strain amounting to 22.2% total strain (11.1% on the inner radius and 11.1% on the outer radius); all compressive strain resulting in 20% total strain; all tensile strain resulting in 25% total strain; or any strain amount there between.

In accordance with the present disclosure, the circumferential stiffness of the balloon wall 110 is sufficiently high to facilitate control of the maximum diameter at the rated burst pressure. In accordance with various embodiments, the balloon wall 110 can comprise a circumferential stiffness of at least 200 gf/mm/mm for 8 mm balloons and 100 gf/mm/mm for 4 mm balloons. In various embodiments, the balloon wall 110 comprises a circumferential stiffness and a longitudinal stiffness and wherein the circumferential stiffness is at least 5 times greater than the longitudinal stiffness. In various embodiments, the balance ratio of the material layer can be 3:1 up to 100:1, e.g., at least 10:1. A sufficiently high circumferential stiffness may also facilitate at least partially a preferential failure mode at the ends of the balloon 100, typically at its seals 104 and/or 105.

To construct the material layer in the desired orientation, the material of the balloon wall 110 can comprise an oriented anisotropic film. Orientation refers to the general direction of the microstructure features, e.g., the fibrils. In various embodiments, the wall 110 comprises a material that is helically oriented at a high angle. For example, the material of wall 110 can have a fibril orientation of at least 75 degrees relative to the longitudinal axis of balloon 100; and in further embodiments, the material of wall 110 can have a fibril orientation of between 80 degrees to 86 degrees. In this instance, the anisotropic film being wrapped at a high angle comprises a high strength in the direction that is oriented at the high wrap angle (in other words, the higher strength of the balloon wall 110 is generally oriented around the circumference and the weaker direction is generally oriented along the length of the balloon).

In accordance with the present disclosure, the material of balloon wall 110 can become plastically deformed upon inflation to a pressure within the working pressure range such that when inflated in a curved configuration defined by a bend radius and requiring 16% strain, the balloon 100 upon re-inflation, without any surrounding constraints and again to a pressure within the working pressure range, will have a curved configuration that comprises a bend radius that is less than 200% larger than the initial bend radius or less than 150% larger than the initial bend radius. In addition, upon re-inflation, the diameter of the balloon will remain within the semi-compliant to non-compliant range.

The described medical balloon can have any appropriate dimension for the clinical application and can be generally cylindrical along the working length 101. The working length 101 of the balloon 100 can be about 10 mm to about 150 mm or more. Similarly, the diameter of the balloon 100 can be about 2 mm to about 30 mm or more. By way of example, a balloon 100 can have a 4 mm diameter and a 30 mm working length, or alternatively, an 8 mm diameter and about a 60 mm working length. Of course, the balloon 100 of the present disclosure can be constructed at any dimensions appropriate for the specific use.

The described medical balloon 100 mounted on an elongate member 150, such as a catheter or a hypotube, can have good trackability through the vasculature. In various embodiments, the described medical balloon 100 can be concentrically crushed to a profile for delivery as opposed to being longitudinally pleated and folded thus having random, numerous, and relatively smaller folds and creases. While not wishing to be bound by any particular theory, it is believed that the longitudinal pleats result in added longitudinal rigidity to the corresponding section of the elongate member 150, whereas random folds in a variety of directions contribute less to the longitudinal rigidity.

The described medical balloon 100 can be used for a number of applications traditionally performed by other semi-compliant to non-compliant balloons. Medical balloon 100 can be used to perform a PTA procedure, deploy or seat a medical device, deliver a drug, deliver RF energy, and/or in any other procedure that would benefit from its properties. When used to deploy, seat, touch-up, or otherwise position medical devices, the described balloon can be used in conjunction with any such devices, such as balloon expandable or self-expanding stents or stent grafts, or other endoluminal devices.

Figure 1D:
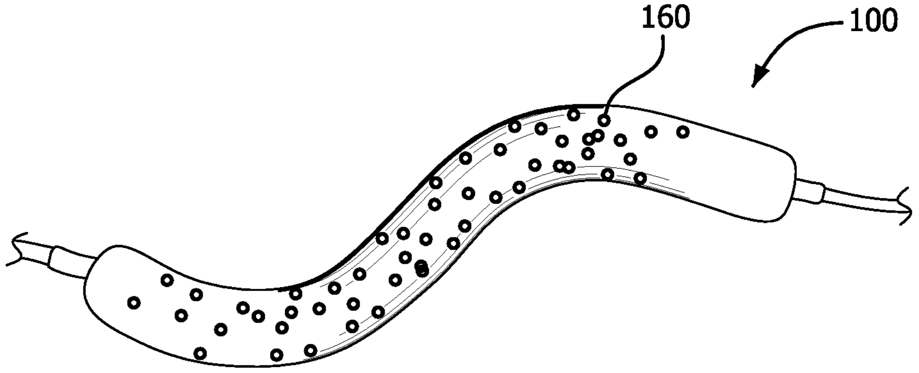
FIG. 1*d* illustrates a medical balloon embodiment in accordance with a present disclosure, inflated in a curved configuration and having a therapeutic agent coated thereon.

By way of example, with reference to FIG. 1*d*, the balloon 100 in accordance with the present disclosure can be coated with a therapeutic agent 160. In further embodiments, a retractable sheath (not shown) can be located about the balloon 100 to prevent or minimize release of said therapeutic agent 160 until the balloon 100 is at the desired treatment site.

A "therapeutic agent," as used herein, is an agent that can a bioactive response or be detectable by an analytical device. Such agents include, but are not limited to, radiopaque compounds, cilostazol, everolimus, dicumarol, zotarolimus, carvedilol, anti-thrombotic agents such as heparin, heparin derivatives, urokinase, and dextrophenylalanine proline arginine chloromethylketone; anti-inflammatory agents such as dexamethasone, prednisolone, corticosterone, budesonide, estrogen, sulfasalazine and mesalamine, sirolimus and everolimus (and related analogs), anti-neoplastic/antiproliferative/anti-miotic agents such as major taxane domain-binding drugs, such as paclitaxel and analogues thereof, epothilone, discodermolide, docetaxel, paclitaxel protein-bound particles such as ABRAXANE® (ABRAXANE is a registered trademark of ABRAXIS BIOSCIENCE, LLC), paclitaxel complexed with an appropriate cyclodextrin (or cyclodextrin like molecule), rapamycin and analogues thereof, rapamycin (or rapamycin analogs) complexed with an appropriate cyclodextrin (or cyclodextrin like molecule), 17β-estradiol, 17β-estradiol complexed with an appropriate cyclodextrin, dicumarol, dicumarol complexed with an appropriate cyclodextrin, β-lapachone and analogues thereof, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; anesthetic agents such as lidocaine, bupivacaine and ropivacaine; anti-coagulants such as D-Phe-Pro-Arg chloromethyl ketone, an RGD peptide-containing compound, AZX100 a cell peptide that mimics HSP20 (Capstone Therapeutics Corp., USA), heparin, hirudin, antithrombin compounds, platelet receptor antagonists, anti-thrombin antibodies, antiplatelet receptor antibodies, aspirin, prostaglandin inhibitors, platelet inhibitors and tick antiplatelet peptides; vascular cell growth promoters such as growth factors, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; protein kinase and tyrosine kinase inhibitors (e.g., tyrphostins, genistein, quinoxalines); prostacyclin analogs; cholesterol-lowering agents; angiopoietins; antimicrobial agents such as triclosan, cephalosporins, aminoglycosides and nitrofurantoin; cytotoxic agents, cytostatic agents and cell proliferation affectors; vasodilating agents; agents that interfere with endogenous vasoactive mechanisms; inhibitors of leukocyte recruitment, such as monoclonal antibodies; cytokines; hormones or a combination thereof. In one embodiment, said therapeutic agent is a hydrophilic agent. In another embodiment, said therapeutic agent is a hydrophobic agent. In another embodiment, said therapeutic agent is paclitaxel.

Figure 1E:
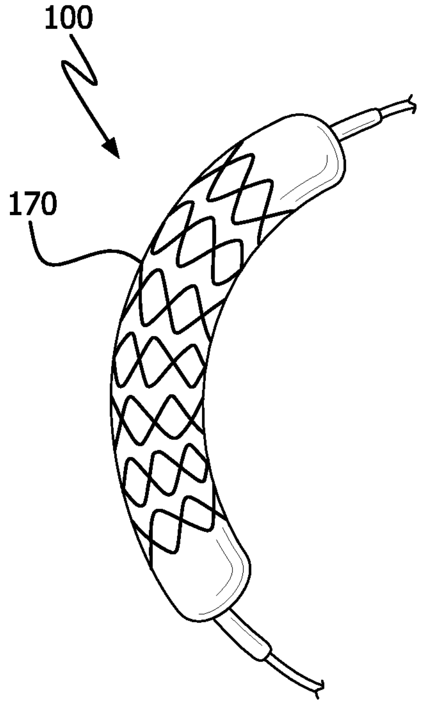
FIG. 1*e* illustrates a medical balloon embodiment in accordance with a present disclosure, inflated in a curved configuration and having a medical device disposed about said medical balloon.

By way of second example, with reference to FIG. 1*e*, balloon 100 in accordance with the present disclosure can comprise medical device 170 disposed about balloon 100. Balloon 100 can be used to expand or touch up medical device 170. As shown, medical device 170 is a stent, and more particularly a segmented stent, e.g., a stent comprising a plurality of discrete annular stent members. As previously mentioned, the stent can be balloon-expandable or self-expanding.

In various embodiments, again with reference to FIGS. 1*a* to 1*c*, the medical balloon 100 comprises a generally cylindrical form that is secured to the elongate member 150 at its proximal and distal ends. The balloon 100 has a body portion 101 across the intermediate section, which is also be referred to as the working length. This section is the section of the balloon 100 that reaches the nominal diameter in the inflated state. The balloon proximal shoulder 102 and distal shoulder 103 are the sections of the balloon 100 lying between the proximal seal 104 and distal seal 105 and the body portion 101. In various embodiments, the shoulders 102, 103 are not conical in shape but are more akin to a rounded corner of a square. In various other embodiments, the shoulders 102, 103 comprise a conical shape or conical stepped shoulders. For example, shoulder 102, 103 of material layer can comprise a non-distensible material that gives the shoulders a conical shape or a stepped conical shape. Radiopaque markers or other detectable marker mechanisms can be used to indicate the working length 101 of the balloon 100. The markers can be located on the underlying elongate member 150 or within or on the balloon wall 110.

In various embodiments, the balloon 100 can further comprise a compliant bladder 120, such as an elastomeric bladder to facilitate a fluid tight device. In various embodiments, the compliant bladder 120 can be detached from wall 110 along at least a portion of the length including the working length 101 and shoulders 102 and 103 or the entire length. In other embodiments, the compliant bladder 120 is attached to the wall 110 along at least a portion of said length or the entire length. The compliant bladder 120 can be an inner layer about which the material layer is situated. The compliant bladder can possess properties that do not consequentially impact the balloon inflating kink-free in a curved configuration.

Figure 2A:
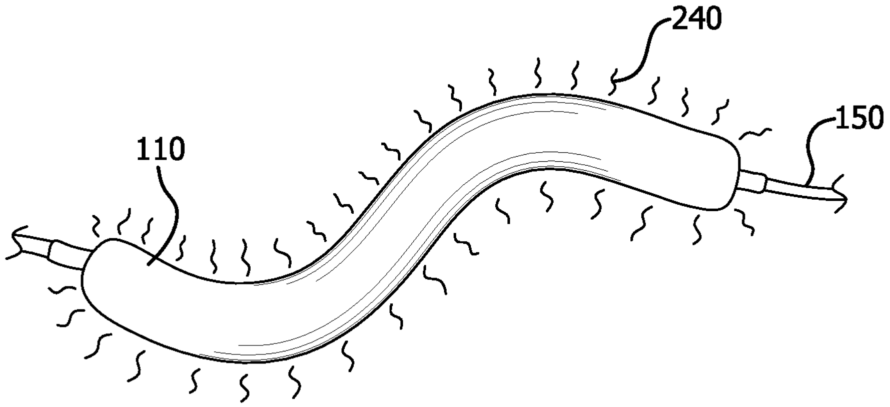
FIG. 2*a* illustrates a perf usable, a medical balloon embodiment in accordance with a present disclosure.
Figure 2B:
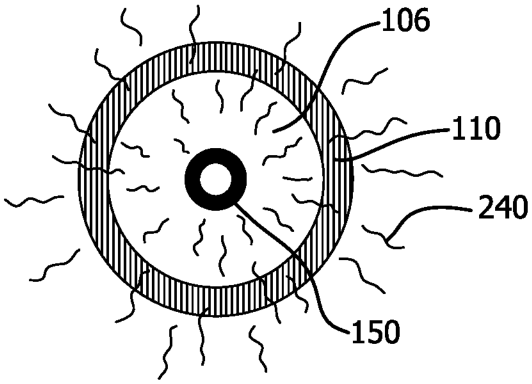
FIG. 2*b* illustrates a schematic view of the cross-section of a perf usable, medical balloon embodiment in accordance with the present disclosure.

In various embodiments, with reference to FIGS. 2*a* to 2*b*, the balloon 100 does not have a compliant bladder and thus is capable of perfusion. For example, balloons 100 are disclosed that expand to a nominal diameter and perfuse in response to an internal pressure exceeding a threshold pressure. In such a manner, in various embodiments, the balloon 100 can be inflated to a first pressure sufficient for the balloon 100 to reach the nominal diameter. Then, at a desired time, the internal pressure can be increased from the first pressure, causing perfusion of the inflation fluid 240 through the balloon wall 110 without a significant increase in balloon diameter. Stated another way, balloons, in accordance with various embodiments, have a water entry pressure ("WEP") and/or bubble point tailored to be at or above that which is required for inflation to a fixed diameter. For example, in various embodiments, the balloon 100 can inflate to a nominal diameter at a pressure below the WEP and/or bubble point and then additional internal pressure can be exerted to reach or exceed the WEP and/or bubble point. Thus, expansion and perfusion can be independently controllable. In various embodiments, the inflation fluid can comprise a therapeutic fluid 240.

Figure 3A:
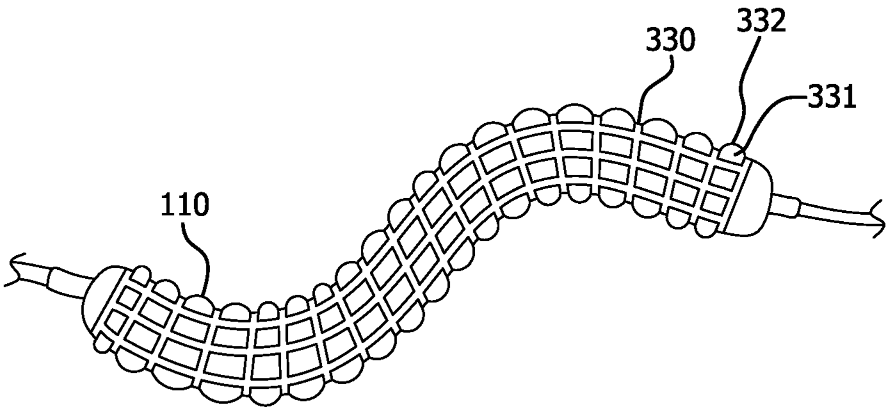
FIG. 3*a* illustrates a medical balloon embodiment in accordance with a present disclosure adapted to form protrusions on the outer surface.
Figure 3B:
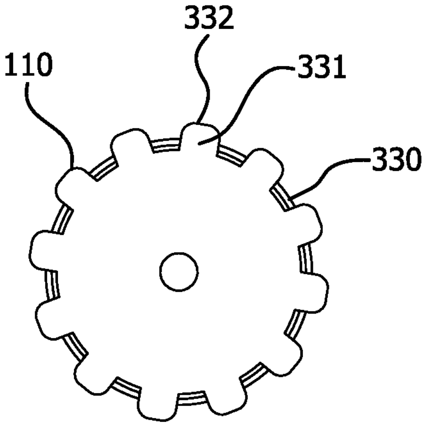
FIG. 3*b* illustrates a schematic view of the cross-section of a medical balloon embodiment in accordance with a present disclosure adapted to form protrusions on the outer surface.

In various embodiments, with reference to FIGS. 3*a* to 3*b*, the balloon 100 can further comprise a template 330 having at least one aperture 331 and overlying at least a portion of the balloon wall 110 wherein the balloon wall 110 protrudes through the aperture 331 in an inflated configuration, producing protrusion 332. The template 330 can similarly be anisotropic, except the template 330 comprises the same or a slightly higher amount of longitudinal stiffness and/or a circumferential stiffness greater than that of the balloon wall 110. As such, the template 330 will expand and/or elongate at a lower rate per increase in internal pressure, thereby resulting in the underlying balloon 100 to protrude through the aperture(s) 331. Alternatively or in addition thereto, the template 330 can have a "nominal diameter" that is less than the underlying balloon 100. The difference between the nominal diameters being the approximate height of a protrusion 332. For example, the template 330 can be similarly formed from a wrapped film as described herein; however, the film is wrapped to form a tubular precursor at a diameter less than the diameter at which the tubular precursor of balloon 100 can be formed. The apertures 331 can be formed in the template 330 in any suitable manner, e.g., laser cutting the tubular precursor.

Aperture 331 can comprise an opening or weakened site in the template 330. In this regard, an opening can be a hole, cut, or any other discontinuous section of the template 330. For example, a hole could be formed by puncturing template 330. Alternatively, aperture 331 can comprise an area of template 330 where a portion of the template material has been removed or otherwise weakened such that the weakened portion at least partially deforms or detaches in response to inflation of balloon 100 and permits distension beyond the first inflated state. Apertures 331 can be formed by any suitable means, including cutting, stamping, laser cutting, perforating, and/or punching/puncturing and/or the like. In various embodiments, the template 330 can comprise a net like structure. The template 330 can comprise apertures 331 that vary in size or are the same size. In addition, decreasing the size the apertures can allow for a "coarser" balloon surface.

Figure 4:
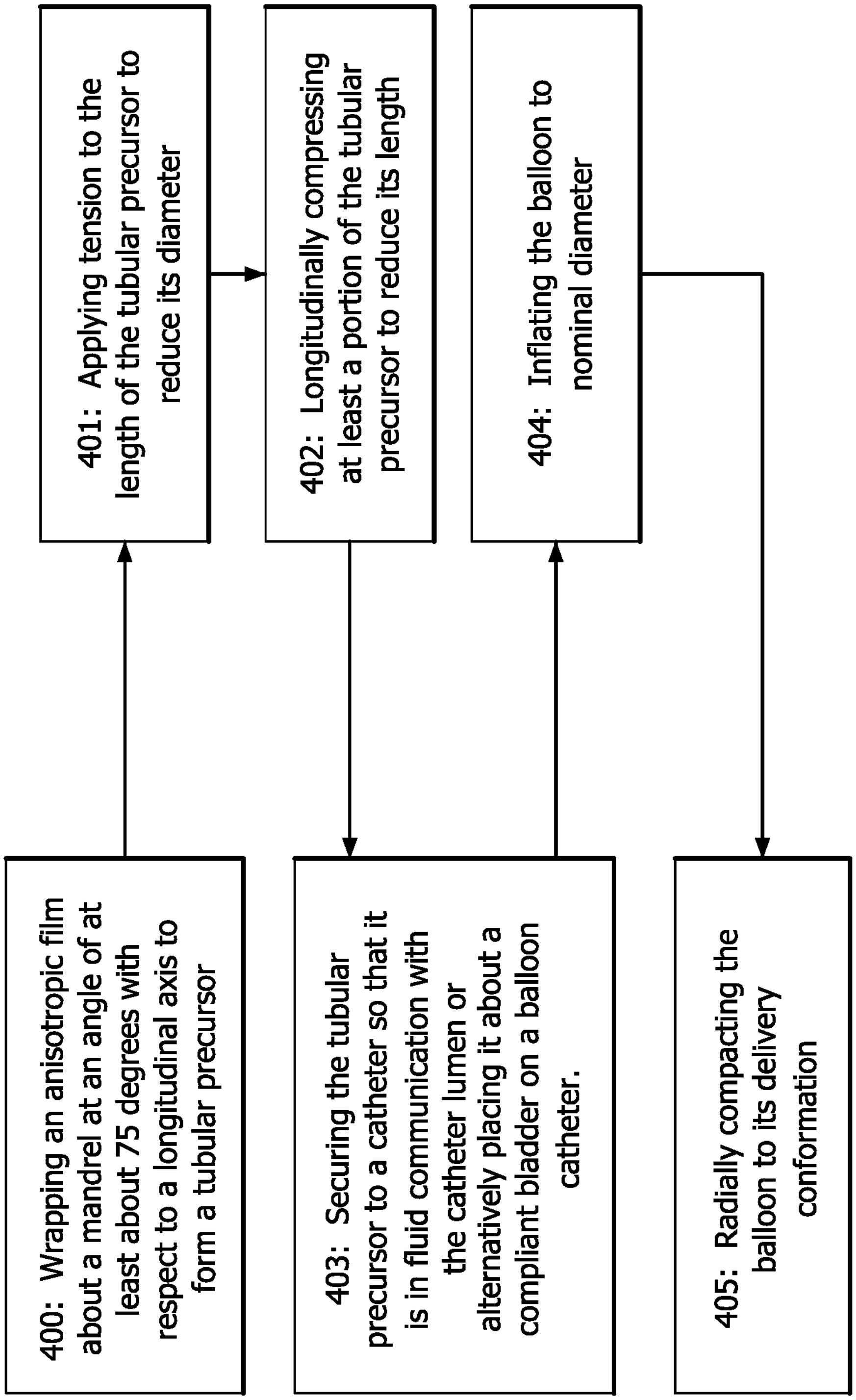
FIG. 4 illustrates a method of making a medical balloon embodiment in accordance with a present disclosure.

With reference to FIG. 4, a method of making a medical balloon in accordance with the present disclosure can comprise wrapping a film about a mandrel at an angle at least about 75 degrees with respect to a longitudinal axis and up to about 88 degrees to form a tubular precursor (400). The wrapped film can be bonded and then removed as a tubular precursor from said mandrel. Once formed, tension to the length of the tubular precursor can be applied to reduce its diameter (401). In various embodiments, at least a portion of the tubular precursor can then be longitudinally compressed to reduce its length (402). The precursor can then be placed on an elongate member having a lumen wherein the precursor is in fluid communication with the lumen of the elongate member and secured thereto (403). The tubular precursor can optionally be secured over a balloon catheter comprising a compliant bladder.

A pre-conditioning inflation can be performed by inflating the balloon to a nominal diameter (404). The inflation can be performed within a concentric tubular form having an inner diameter approximately equal to the nominal diameter of the balloon. The balloon and the balloon cover can be radially compacted to a delivery profile (405). The radial compaction of the balloon cover forms random creases and folds in random directions.

Figure 5:
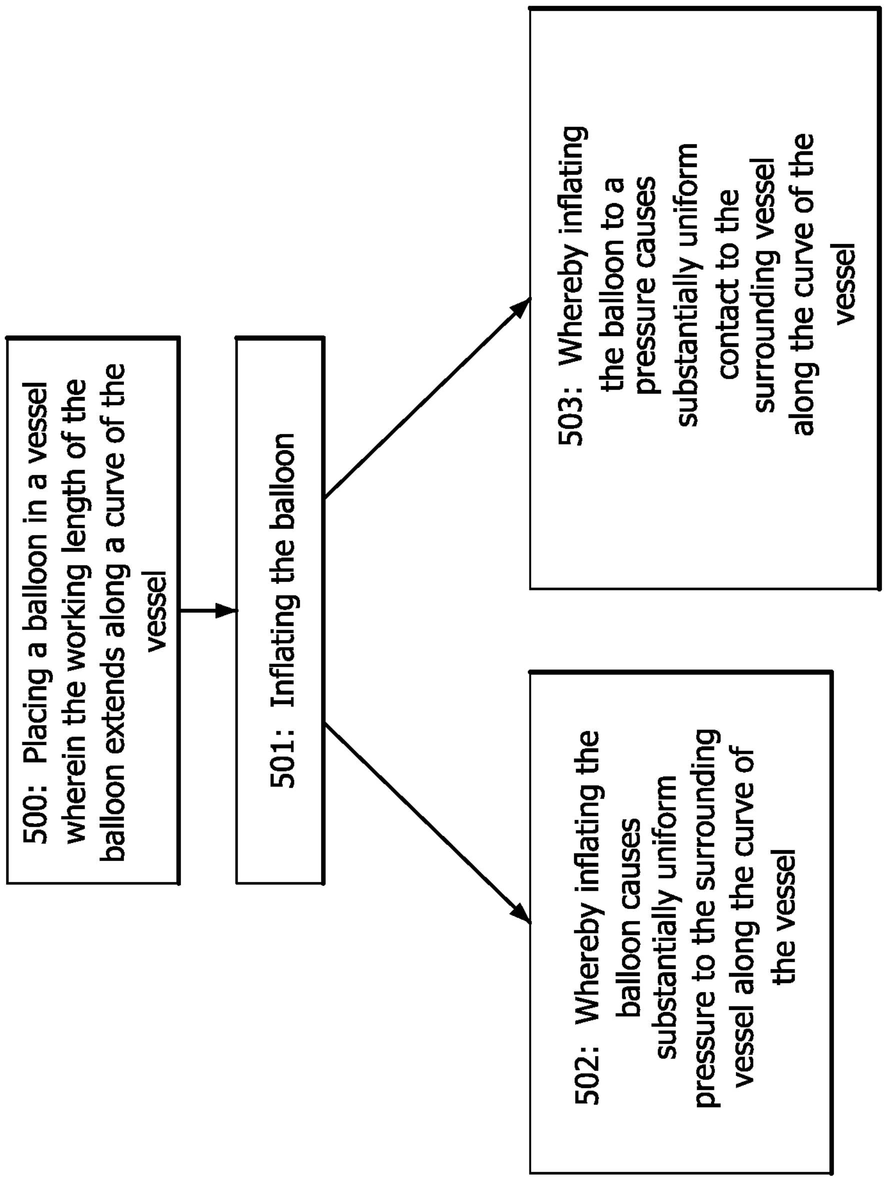
FIG. 5 illustrates a method of using a medical balloon embodiment in accordance with a present disclosure.

With reference to FIG. 5 a method of using a medical balloon in accordance with the present disclosure can comprise placing a balloon as described herein in a vessel wherein the working length of the balloon extends along a curve of the vessel (500). The curvature of the vessel would cause at least 20% total strain to the balloon wall and the balloon wall along an inner arc would have at least 5% compressive strain upon inflation. Once in position, the balloon can be inflated (501) to at least 4 atm, at least 8 atm, at least 16 atm, at least 20 atm, or more, or any range or value therebetween. In various embodiments, inflating the balloon causes substantially uniform pressure to be applied to the surrounding vessel along the curve of the vessel (502). In various embodiments, inflating the balloon causes substantially uniform contact to the surrounding vessel wall along the curve of the vessel (503).

Example 1—Precursor Material

An expanded PTFE membrane—that is amorphously locked and generally made in accordance with U.S. Pat. No. 5,476,589 to Bacino which is hereby incorporated by reference in its entirety—had the following properties: Bubble point is approximately 138 kPa, thickness is approximately 6.3 μm, mass per area is approximately 3 g/m2, matrix tensile strength in the strongest direction is approximately 907 mPa, matrix tensile strength in the direction orthogonal to the strongest direction is approximately 17.2 mPa. The precursor material was cut into a tape, wherein the strongest direction is along the length of the tape.

Example 2—Constructing Medical Balloon Comprising a Nominal Diameter of 8 mm in Accordance with the Present Disclosure A tubular precursor was formed as follows: The precursor material from Example 1 having a 1.25 in slit width was helically wrapped about an 8.5 mm mandrel at approximately 85 degrees relative to the longitudinal axis of the mandrel. The wraps were repeated on a bias in the opposite direction to complete a total of four passes over a length of 100 mm. This tubular precursor was then thermally treated in an oven at 380° C. for 11 minutes and then removed from the oven. The tubular precursor was removed from the mandrel and axially stretched to decrease its diameter to about 1.8 mm. The tubular precursor was then placed on a mandrel having an outer diameter of about 1.8 mm and cut to 108 mm. The tube assembly was then axially compressed to about 72% of its original length.

A compliant polyurethane balloon catheter was obtained with a generally cylindrical balloon having a diameter of 5 mm and length of 60 mm (Bavaria Medizin Technologie GmbH (BMT), Oberpfaffenhofen, Germany). The tubular precursor was slid over the balloon assembly (with the balloon in its collapsed state). The ends of the tubular precursor were secured to the catheter using LOCTITE® adhesive 4981 (Henkel Corporation, Düsseldorf, Germany) applied to an approximately 6 mm wide ePTFE tape as it was wrapped 15 times about the ends and the catheter body. The balloon was then inflated to an approximate 8 mm diameter at 16 atmospheres. With inflation medium in the balloon and the inflation valve open, the tubular precursor, now a balloon cover, and compliant bladder were then radially compacted at 689 kPa to about the catheter.

Example 3—Compressive and Tensile Strain Test Method and Results

Test method: First, a 0.9 mm PTFE coated stainless steel mandrel was inserted through the lumen of the balloon catheter to be tested. The balloon was inflated to nominal inflation pressure. The inflation valve was closed. The exterior surface of the working length of the balloon was measured and marked around its circumference at 10 mm intervals. The inflation valve was then opened and the balloon allowed to deflate. The mandrel was removed and replaced with a 0.035" guidewire (AMPLATZ SUPER STIFF® Guidewire, Boston Scientific, Natick, MA, USA), ensuring that the flexible section of the guidewire was beneath the balloon portion of the catheter.

Figure 6A:
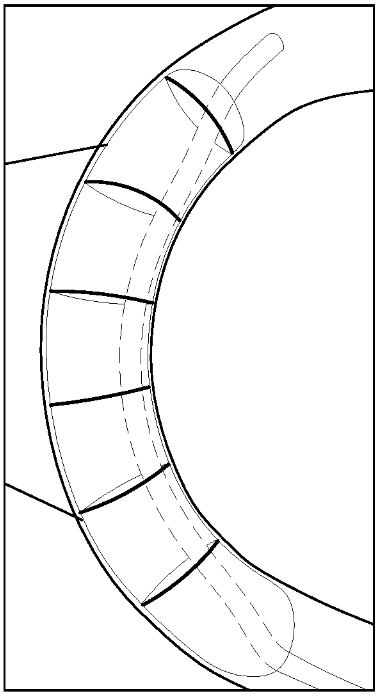
FIGS. 6*a*-6*c* depict images of a nylon balloon in a bent configuration as described in Example 3.
Figure 6C:
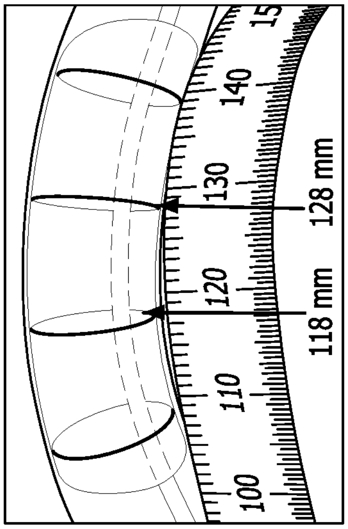
Figure 6B:
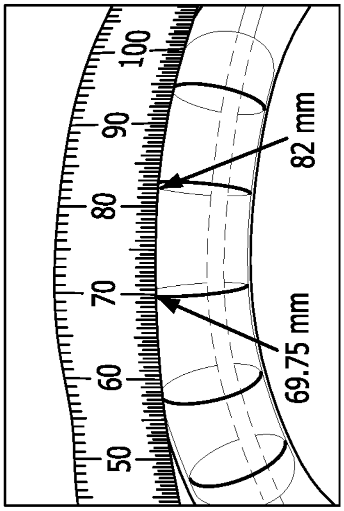
Figure 7A:
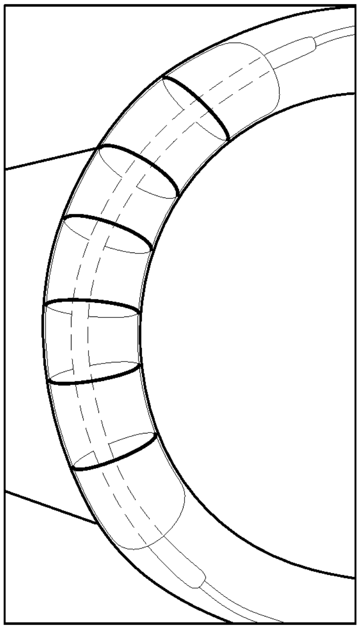
FIGS. 7*a*-7*c* depict images of a medical balloon embodiment in accordance with a present disclosure in a bent configuration as described in Example 3.
Figure 7B:
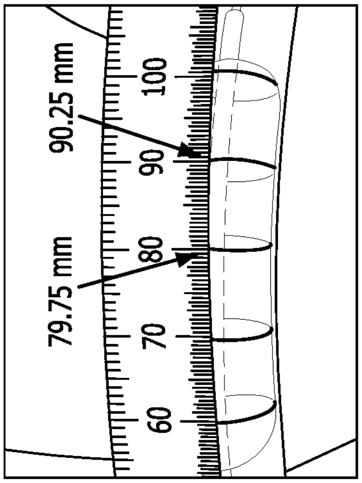
Figure 7C:
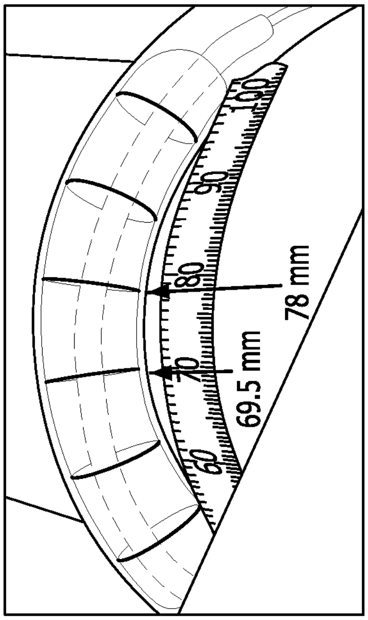

The balloon to be tested was then inserted into an 8 mm ID×12 mm OD polyurethane tubing (Part number 50315K281, McMaster-Carr, Santa Fe Springs, CA, USA). The area in which the balloon was to be positioned within the tube was lubricated with a light coat of release compound (Release Compound 7, Dow-Corning, Elizabethtown, KY). The polyurethane tubing was bent around a 60 mm diameter rod while holding the tubing tight against the outside circumference so that the balloon was centered in the bent section of the tubing as shown in FIGS. 6*a*-6*c* and 7*a*-7*c*. The balloon was inflated within the tube to its rated burst pressure. A flexible ruler was bent around the rod adjacent the tube and the spacing of the marks on the balloon on the inside arc of the bend were measured, as shown in FIGS. 6*c* and 7*c*. The flexible ruler was similarly used to measure the marks across the outside arc of the balloon, as shown in FIGS. 6*b* and 7*b*. The measurements obtained are provided in Table 1.

TABLE 1

| Balloon | Balloon Pressures | Distance between marks on the outside arc | Distance between marks on the inside arc | Compressive Strain on inside arc | Tensile Strain on outside arc |
|---|---|---|---|---|---|
| 8 mm × 62 mm standard BMT PTA balloon (Nylon, Lot 130327) | 16 atm | 12.25 mm (See FIG. 6b) | 10 mm (See FIG. 6c) | 0% | 22.5% |
| 8 mm × 60 mm balloon prepared in accordance with Example 2) | 16 atm | 10.5 mm (See FIG. 7b) | 8.5 mm (See FIG. 7c) | 15% | 5% |

Compressive strain was detected on the balloon made in accordance with Example 2, while none was detected on the BMT PTA balloon (Bavaria Medizin Technologie GmbH (BMT), Oberpfaffenhofen, Germany).

Example 4—Method for Calculating Theoretical Compressive and Tensile Strain

Figure 10:
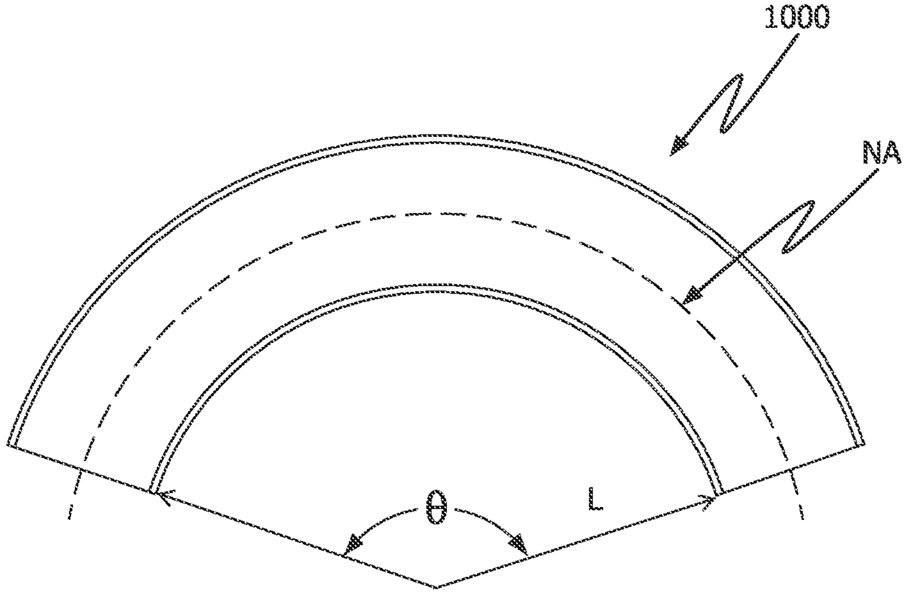
FIG. 10 is a schematic curve as described in Example 3.
Figure 11A:
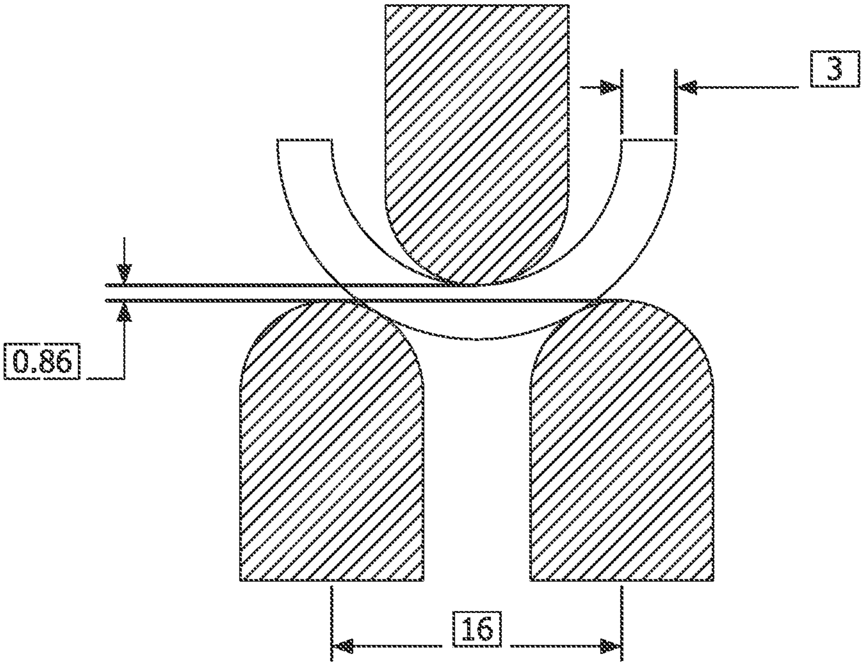
FIGS. 11*a*-11*d* illustrate the setup of the Instron 3-point bend fixture for a 3 mm, a 5 mm, an 8 mm, and a 12 mm balloon, respectively.
Figure 11B:
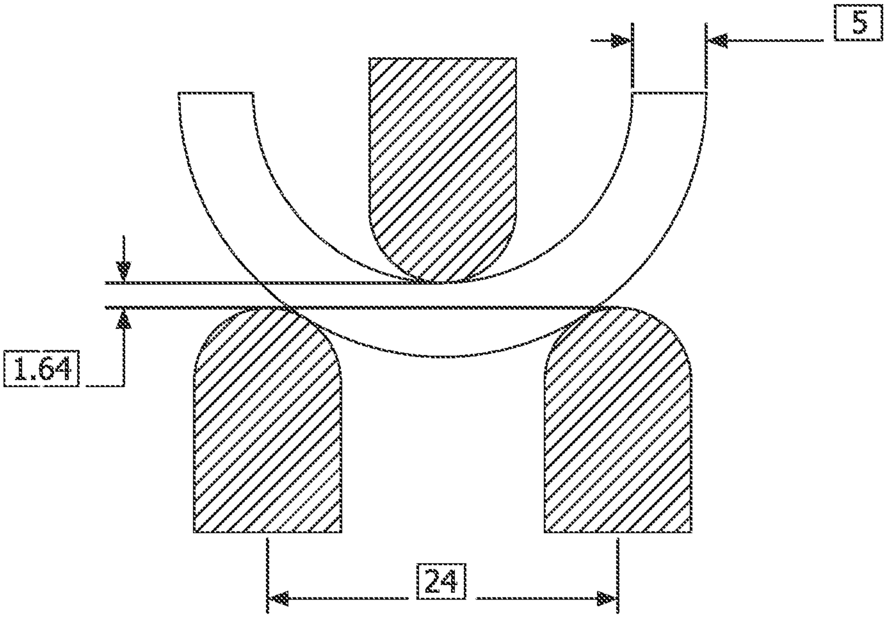
Figure 11C:
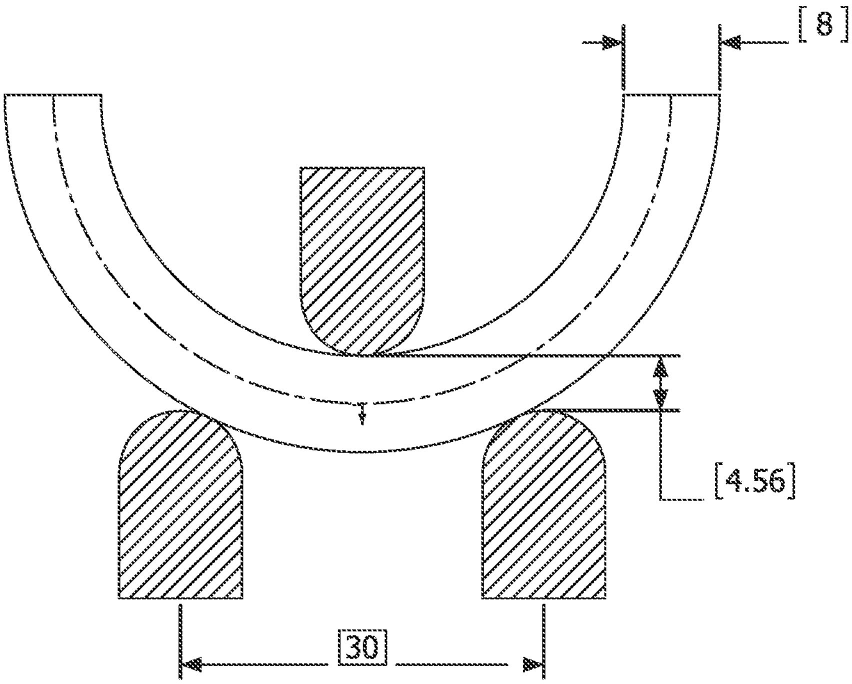
Figure 11D:
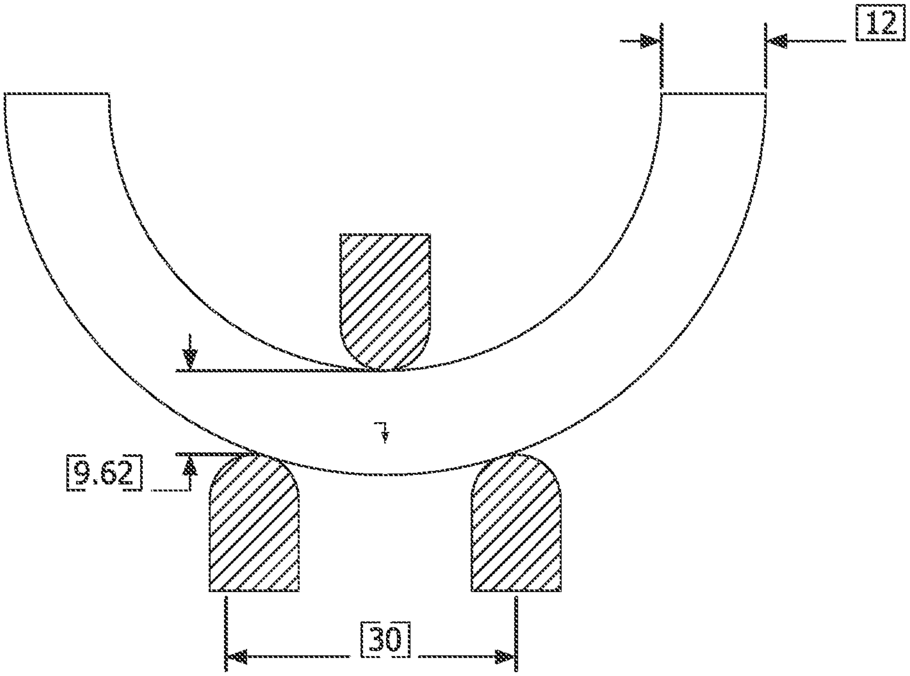

In order to obtain perspective on the strain values observed in Example 3, the theoretical strain values required to maintain a neutral axis can be compared to the observed values. The theoretical compressive and tensile strain values can be calculated based on the following. FIG. 10 is a schematic of the test setup described in Example 3. Tubing 1000 is shown in a bent configuration. Neutral axis "NA" lies co-radially with tubing 1000. When a balloon having a catheter aligned co-radially is inserted into the tube 1000, the center axis of the balloon will match this neutral axis. The working length of the balloon will have an arc length aligned along the neutral axis. The angle θ is calculated according to this formula:

$\theta = S/r$, where $S$ is the arc length, $r$ is the radius, and theta is the angle in radians.

Using this approach, 6 equals 1.56 radians if a balloon having a working length of 50 mm is inserted into the test apparatus and the bend has a radius of 32 mm (includes the wall thickness of tubing 1000).

To solve for the arc radius on the inside length of the balloon $S_i$ (under compression) and the outside length of the balloon $S_o$ (under tension) the following relationship is used:

$$S_1/r_1 = \theta = S_2/r_2$$

For a balloon having a diameter of 8 mm and a 50 mm working length with a bend radius of 32 mm, assuming equal amounts of compressive and tensile strain, the inside arc length $S_i$ is calculated by the following: 32*50/(32+4)= $S_i$=44.44 mm. For the same balloon and radius, the outer arc length $S_o$ is calculated by the following: (32+8)*50/(32+4)= $S_o$=55.56 mm. Therefore, $S_o$ is 11.1% longer than the working length of the balloon along the neutral axis and $S_i$ is 11.1% shorter than the working length of the balloon along the neutral axis.

Through a similar calculation, assuming all compressive strain, the total strain would be 20%, and when assuming all tensile strain, the total strain would be 25%. The 25% total strain on the outer arc is close to that which was observed for the PTA Nylon balloon test in Example 3 at 22.5%.

Example 5—Method of Determining the Longitudinal and Circumferential Stiffness of a Balloon Wall and Test Results Test Method: The balloon to be tested was inflated by placing a 100 mm section of drawn ePTFE tubing over a pleated and folded balloon (8 mm×60 mm) to form a cover. Movement of the cover was limited during inflation by ensuring cover material was clamped in a vice that was supporting/clamping the catheter. The balloon was inflated and the mid-balloon diameter was recorded with a laser micrometer. Once a diameter of 8 mm was achieved, the balloon was deflated. The cover is removed from the balloon.

Next, for each longitudinal sample the cones of the balloon were cut so that the sample was 50 mm long. The cuts were located in the flat working length of the balloon and resulted in square edges. Each sample was longitudinally slit with scissors to form a sheet and then trimmed to create a sample that was 50 mm long×20 mm wide. An INSTRON® tensile tester was set up with smooth grips, and the jaw pressure was set to 552 kPa. The rate was set to 10 mm/min with a gauge length of 10 mm. Prior to loading the sample in the INSTRON® device, the width was taken in the middle of the sample length. The gauge length of the specimen during the testing was 10 mm. The test was set to run for 1 mm of crosshead displacement (~10% strain). The resulting slope (i.e., force over change in length) was divided by the specimen width to obtain the stiffness, as this response is not normalized per specimen thickness or % strain. The slope was calculated in the region that matches the balloon tested “longitudinal” compliance. For example, if a balloon had a 3% longitudinal compliance (i.e., the percent of balloon lengthening when inflated from the nominal inflation pressure to the rated burst pressure), the slope would be determined within the 3% strain region.

For each circumferential sample, after inflating the balloon as described above, the cones of the balloon were cut within the flat working length of the balloon but maximizing the sample length and resulting in square edges. The sample was further cut to form 2 annular samples, each with a length of 10 mm. The INSTRON® device was set with a circumferential fixture. The rate was set to 10 mm/min and the gauge length was set so that the fixtures were almost in contact with each other. The test was set to run for 1 mm of crosshead displacement (~8% strain). This resulting slope (i.e., force over change in length) was divided by the specimen width and multiplied by 2 to account for the hoop specimen to determine stiffness, as this response was not normalized per specimen thickness or % strain. The slope was calculated in the region that matches the balloon tested compliance. For example, if a balloon had a 3% circumferential compliance (i.e., the percent of circumferential diametric growth of the balloon when inflated from the nominal inflation pressure to the rated burst pressure), the slope would be determined within the 3% strain region.

The above tests were performed on the following balloons: High Pressure PTA Catheter, Creagh Medical Ltd, Galway, Ireland; “Fox” Balloon Catheter, p/n 12760-06, Abbott Vascular, Santa Clara, California, USA; “Workhorse” P/N 16500432; PTA Balloon Catheter, AngioDynamics, Latham, NY; 3 conformable balloons prepared in accordance with Example 2 with precursor materials as indicated below. The results are shown in FIG. 8.

Lo MD: An expanded ePTFE membrane—that is amorphously locked and generally made in accordance with U.S. Pat. No. 5,476,589 to Bacino which is hereby incorporated by reference in its entirety—had the following properties: Bubble point is approximately 138 kPa, thickness is approximately 6.3 μm, mass per area is approximately 3 g/m$^2$, matrix tensile strength in the strongest direction is approximately 917 mPa, matrix tensile strength in the direction orthogonal to the strongest direction is approximately 17.2 mPa. The precursor material was cut into a tape of 2.5 cm width, wherein the strongest direction is along the length of the tape.

Med MD: An expanded ePTFE membrane—that is amorphously locked and generally made in accordance with U.S. Pat. No. 5,476,589 to Bacino which is hereby incorporated by reference in its entirety—had the following properties: Bubble point is approximately 138 kPa, thickness is approximately 6.3 μm, mass per area is approximately 3 g/m$^2$, matrix tensile strength in the strongest direction is approximately 834 mPa, matrix tensile strength in the direction orthogonal to the strongest direction is approximately 36.5 mPa. The precursor material was cut into a tape of 2.5 cm width, wherein the strongest direction is along the length of the tape.

Hi MD: An expanded ePTFE membrane—that is amorphously locked and generally made in accordance with U.S. Pat. No. 5,476,589 to Bacino which is hereby incorporated by reference in its entirety—had the following properties: Bubble point is approximately 138 kPa, thickness is approximately 6.3 μm, mass per area is approximately 3 g/m$^2$, matrix tensile strength in the strongest direction is approximately 758 mPa, matrix tensile strength in the direction orthogonal to the strongest direction is approximately 67.6 mPa. The precursor material was cut into a tape of 2.5 cm width, wherein the strongest direction is along the length of the tape.

Figure 9A:
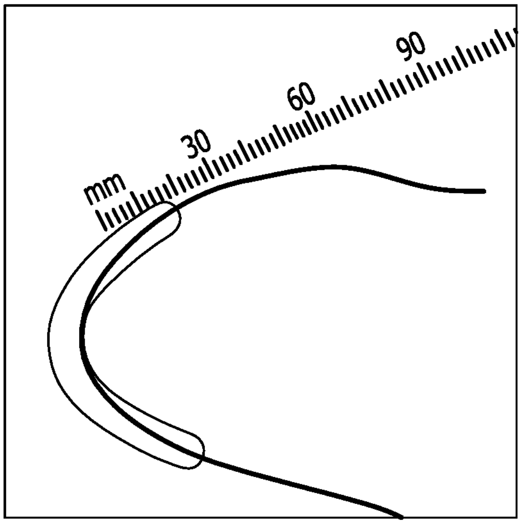
FIGS. 9*a*-9*d* are reproduction sketches of fluoroscopy images of various balloon devices as set forth in Example 6 inflated in a curved vessel. The animal model and vessel location within the animal model (i.e., where the balloon was inflated) were the same for FIGS. 9*a* and 9*d* and for FIGS. 9*b* and 9*c*. As such, the relative amount of vessel deformation (or straightening) can be inferred from the shape of the balloon and the catheter. The conformable balloons of FIGS. 9*a* and 9*b* exhibit a more curved shape and minimal, if not any, vessel straightening. In addition, the shoulders on the conformable balloons of FIGS. 9*a* and 9*b* are not deformed, and the guidewire is generally centered between the shoulders at both ends of the balloon. This is indicative of less stress at the ends as compared to the balloons of FIGS. 9*c* and 9*d*.
Figure 9B:
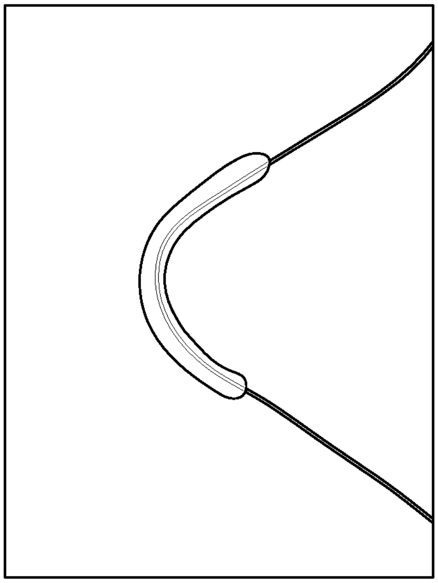
Figure 9C:
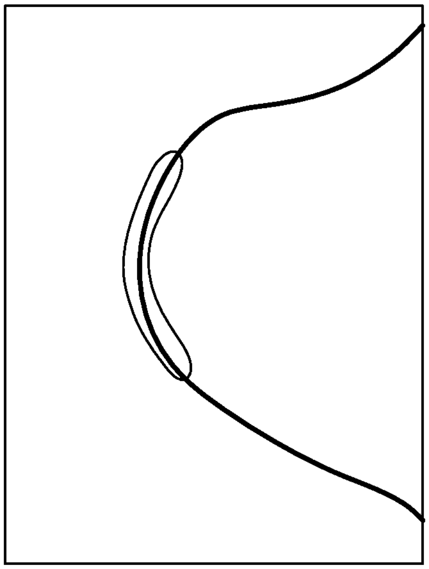
Figure 9D:
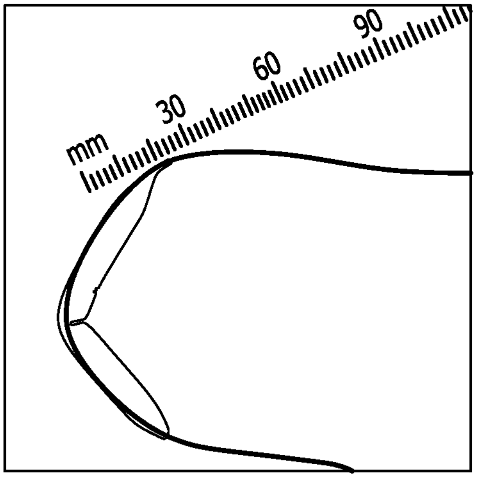

Example 6—In Vivo Inflation of a Medical Balloon within a Curved Vasculature The following balloons were each inflated in the bifurcated iliac of a canine model and the images were taken at the indicated pressures. As shown in FIG. **9*d*, a Conquest balloon (P/N CQ-7586, Bard Medical, Tempe, AZ) was inflated to 10 atm and exhibited a kink in the working length and vessel straightening. The balloon could not be inflated to the rated burst pressure because the observed degree of vessel straightening. As shown in FIG. 9*c*, a semi-compliant balloon was inflated to 8 atm and exhibits vessel straightening. The balloon could not be inflated to the rated burst pressure because the observed degree of vessel straightening. As shown in FIGS. 9*a* and 9*b***, the conformable balloon prepared in accordance with Example 2 exhibited kink-free inflation and improved conformance to the curved vessel at both 10 atm and at 18 atm.

Example 7—Constructing Medical Balloon Comprising a Nominal Diameter of 3 mm in Accordance with the Present Disclosure A tubular precursor was formed as follows: The precursor material from Example 1 at a 0.5 inch slit width was helically wrapped about a 3.25 mm mandrel at 76 degrees relative to the longitudinal axis of the mandrel. The wraps were repeated on a bias in the opposite direction to complete a total of six passes. This tubular precursor was then thermally treated in an oven at 380° C. for 5 minutes and then removed from the oven. The tubular precursor was removed from the mandrel and axially stretched to decrease its diameter to about 1.8 mm. The tubular precursor was then placed on a mandrel having an outer diameter of about 1.8 mm and cut to 87 mm. The balloon working length portion of the tube assembly was then axially compressed to about 90% of its original length.

A compliant polyurethane balloon catheter was obtained with a generally cylindrical balloon having a diameter approximately 5 mm and length of 60 mm (Bavaria Medizin Technologie GmbH (BMT), Oberpfaffenhofen, Germany). The tubular precursor was slid over the balloon assembly (with the balloon in its collapsed state). The ends of the tubular precursor were secured to the catheter using LOCTITE® adhesive 4981 (Henkel Corporation, Düsseldorf, Germany) applied to an approximately 6 mm wide ePTFE tape as it was wrapped 15 times about the ends and the catheter body. The balloon was then inflated to an approximate 3 mm diameter at approximately 10 atmospheres. With inflation medium in the balloon and the inflation valve open, the tubular precursor, now a balloon cover, and compliant bladder were then radially compacted at approximately 689 kPa to about the catheter.

Example 8—Constructing Medical Balloon Comprising a Nominal Diameter of 5 mm in Accordance with the Present Disclosure A tubular precursor was formed as follows: The precursor material from Example 1 having a 1 inch slit width was helically wrapped about a 5.2 mm mandrel at 81 degrees relative to the longitudinal axis of the mandrel. The wraps were repeated on a bias in the opposite direction to complete a total of four passes. This tubular precursor was then thermally treated in an oven at 380° C. for 7 minutes and then removed from the oven. The tubular precursor was removed from the mandrel and axially stretched to decrease its diameter to about 1.8 mm. The tubular precursor was then placed on a mandrel having an outer diameter of about 1.8 mm and cut to 108 mm. The balloon working length portion of the tube assembly was then axially compressed to about 80% of its original length.

A compliant polyurethane balloon catheter was obtained with a generally cylindrical balloon having a diameter of 5 mm and length of 60 mm (Bavaria Medizin Technologie GmbH (BMT), Oberpfaffenhofen, Germany). The tubular precursor was slid over the balloon assembly (with the balloon in its collapsed state). The ends of the tubular precursor were secured to the catheter using LOCTITE® adhesive 4981 (Henkel Corporation, Düsseldorf, Germany) applied to an approximately 6 mm wide ePTFE tape as it was wrapped 15 times about the ends and the catheter body. The balloon was then inflated to an approximate 5 mm diameter at approximately 12 atmospheres. With inflation medium in the balloon and the inflation valve open, the tubular precursor, now a balloon cover, and compliant bladder were then radially compacted at approximately 689 kPa to about the catheter.

Example 9—Constructing Medical Balloon Comprising a Nominal Diameter of 8 mm in Accordance with the Present Disclosure A tubular precursor was formed as follows: The precursor material from Example 1 having a 1.25 inch slit width was helically wrapped about an 8.5 mm mandrel at approximately 85 degrees relative to the longitudinal axis of the mandrel. The wraps were repeated on a bias in the opposite direction to complete a total of four passes. This tubular precursor was then thermally treated in an oven at 380° C. for 11 minutes and then removed from the oven. The tubular precursor was removed from the mandrel and axially stretched to decrease its diameter to about 1.8 mm. The tubular precursor was then placed on a mandrel having an outer diameter of about 1.8 mm and cut to 135 mm. The balloon working length portion of the tube assembly was then axially compressed to about 70% of its original length.

A compliant polyurethane balloon catheter was obtained with a generally cylindrical balloon having a diameter of 5 mm and length of 60 mm (Bavaria Medizin Technologie GmbH (BMT), Oberpfaffenhofen, Germany). The tubular precursor was slid over the balloon assembly (with the balloon in its collapsed state). The ends of the tubular precursor were secured to the catheter using LOCTITE® adhesive 4981 (Henkel Corporation, Düsseldorf, Germany) applied to an approximately 6 mm wide ePTFE tape as it was wrapped 15 times about the ends and the catheter body. The balloon was then inflated to an approximate 8 mm diameter at 16 atmospheres. With inflation medium in the balloon and the inflation valve open, the tubular precursor, now a balloon cover, and compliant bladder were then radially compacted at 689 kPa to about the catheter.

Example 10—Constructing Medical Balloon Comprising a Nominal Diameter of Approximately 12 mm in Accordance with the Present Disclosure A tubular precursor was formed as follows: The precursor material from Example 1 having a 1.25 inch slit width was helically wrapped about a 13 mm mandrel at 86 degrees relative to the longitudinal axis of the mandrel. The wraps were repeated on a bias in the opposite direction to complete a total of six passes. This tubular precursor was then thermally treated in an oven at 380° C. for 17 minutes and then removed from the oven. The tubular precursor was removed from the mandrel and axially stretched to decrease its diameter to about 1.8 mm. The tubular precursor was then placed on a mandrel having an outer diameter of about 1.8 mm and cut to 185 mm. The balloon working length portion of the tube assembly was then axially compressed to about 55% of its original length.

A compliant polyurethane balloon catheter was obtained with a generally cylindrical balloon having a diameter of 5 mm and length of 60 mm (Bavaria Medizin Technologie GmbH (BMT), Oberpfaffenhofen, Germany). The tubular precursor was slid over the balloon assembly (with the balloon in its collapsed state). The ends of the tubular precursor were secured to the catheter using LOCTITE® adhesive 4981 (Henkel Corporation, Düsseldorf, Germany) applied to an approximately 6 mm wide ePTFE tape as it was wrapped 15 times about the ends and the catheter body. The balloon was then inflated to an approximate 12 mm diameter at approximately 5 atmospheres. With inflation medium in the balloon and the inflation valve open, the tubular precursor, now a balloon cover, and compliant bladder were then radially compacted at 689 kPa to about the catheter.

Example 11—Comparison Study of Straightening Force of Medical Balloons as Measured in 3-Point Bend Fixture Test Method: In order to measure the straightening force, an Instron® 3-point bend fixture with an Instron® 100N load cell was set up, such that the balloon to be tested would have a bend radius that would achieve a 16% theoretical strain (according the equation described in Example 4) at the nominal inflation pressure. The setup of the Instron® 3-point bend fixture is shown in FIGS. 11*a* to 11*d* for the 3 mm, 5 mm, 8 mm, and 12 mm balloon, respectively. The dimensions shown in FIGS. 11*a* to 11*d* are in millimeters.

Prior to testing, each balloon was conditioned by submersing in a 37° C. water bath for 2 minutes. Once conditioned, a guidewire (Amplatz, 0.035" Super Stiff) was inserted into to catheter of the balloon such that the "floppy" end was aligned with the balloon portion. A pressure gauge and indeflator was connected to the catheter. The sample was inserted into the 3-point bend fixture in a curved conformation approximate the appropriate bend radius. Each balloon was inflated to pressures spanning the working pressure range and as shown in the table of data provided in FIG. 12. Each balloon was held at each pressure for 10 seconds except for the rated burst pressure, which was held for 30 seconds. The force was measured continuously throughout the entire test with mean force for each pressure provided in FIG. 12. The working pressure range for the 3 mm balloon of Example 7 was 10 atm to 17 atm. The working pressure range for the 5 mm balloon of Example 8 was 9 atm to 17 atm. The working pressure range for the 8 mm balloon of Example 9 was 6 atm to 16 atm. The working pressure range for the 12 mm balloon of Example 10 was 5 atm to 8 atm.

The above test was performed on the following balloons: "Conquest" Balloon Catheter, P/N CQ-7586, Bard Medical, Tempe, AZ; "FoxCross" Balloon Catheter, P/N 10324-80 (3 mm), 10326-60 (5 mm), 10329-60 (8 mm), 10332-60 (12 mm), Abbott Vascular, Santa Clara, California, USA; "Workhorse" P/N 16500432; PTA Balloon Catheter, AngioDynamics, Latham, NY; and 4 balloons prepared in accordance with Examples 7-10.

Figure 13A:
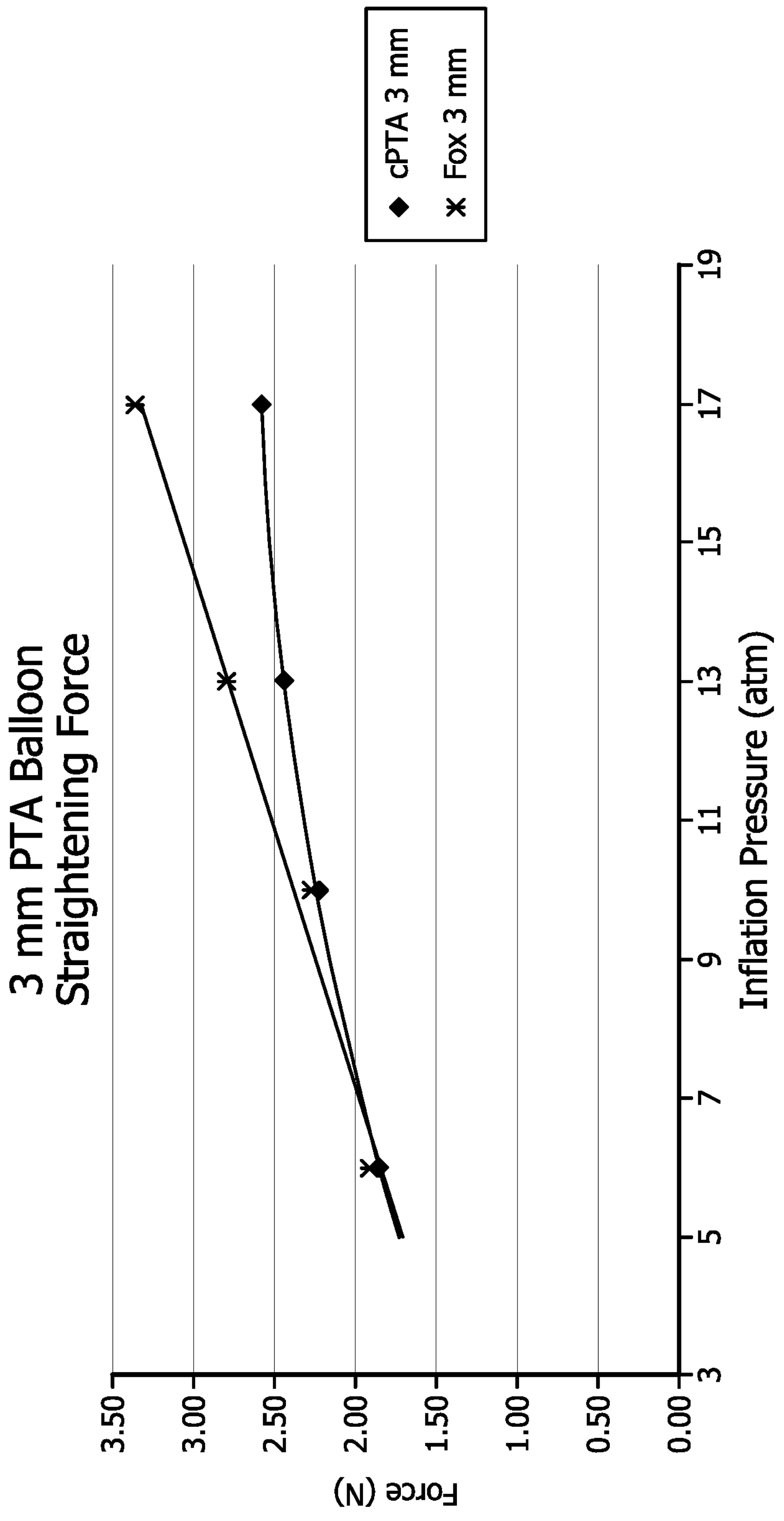
FIG. 13*a* is a plot showing the straightening force as a function of pressure of a 3 mm nominal diameter balloon made in accordance with the present disclosure compared to an Abbott "FoxCross" 3 mm balloon as described in Example 11.
Figure 13B:
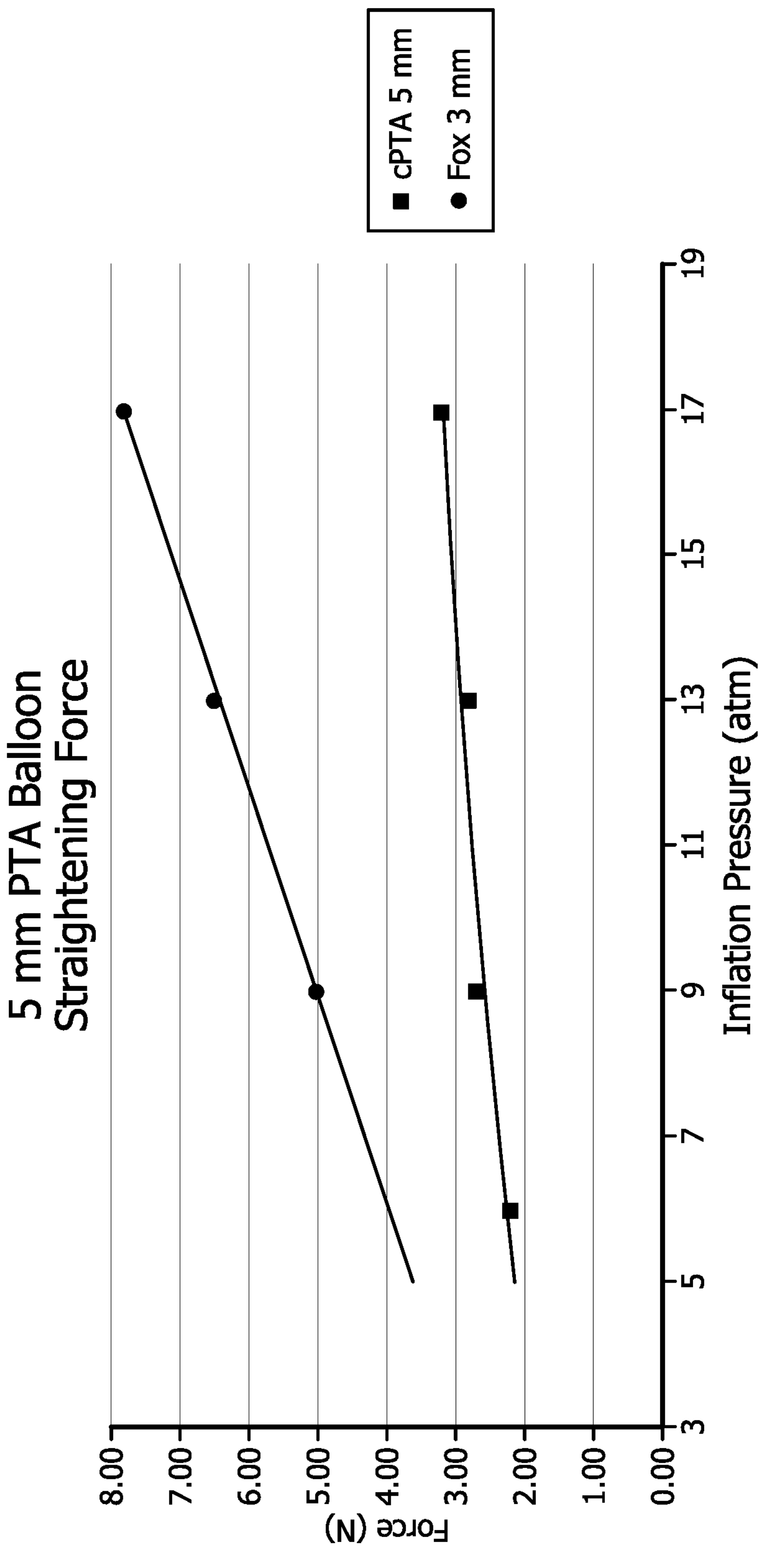
FIG. 13*b* is a plot showing the straightening force as a function of pressure of a 5 mm nominal diameter balloon made in accordance with the present disclosure compared to an Abbott "FoxCross" 5 mm balloon as described in Example 11.
Figure 13C:
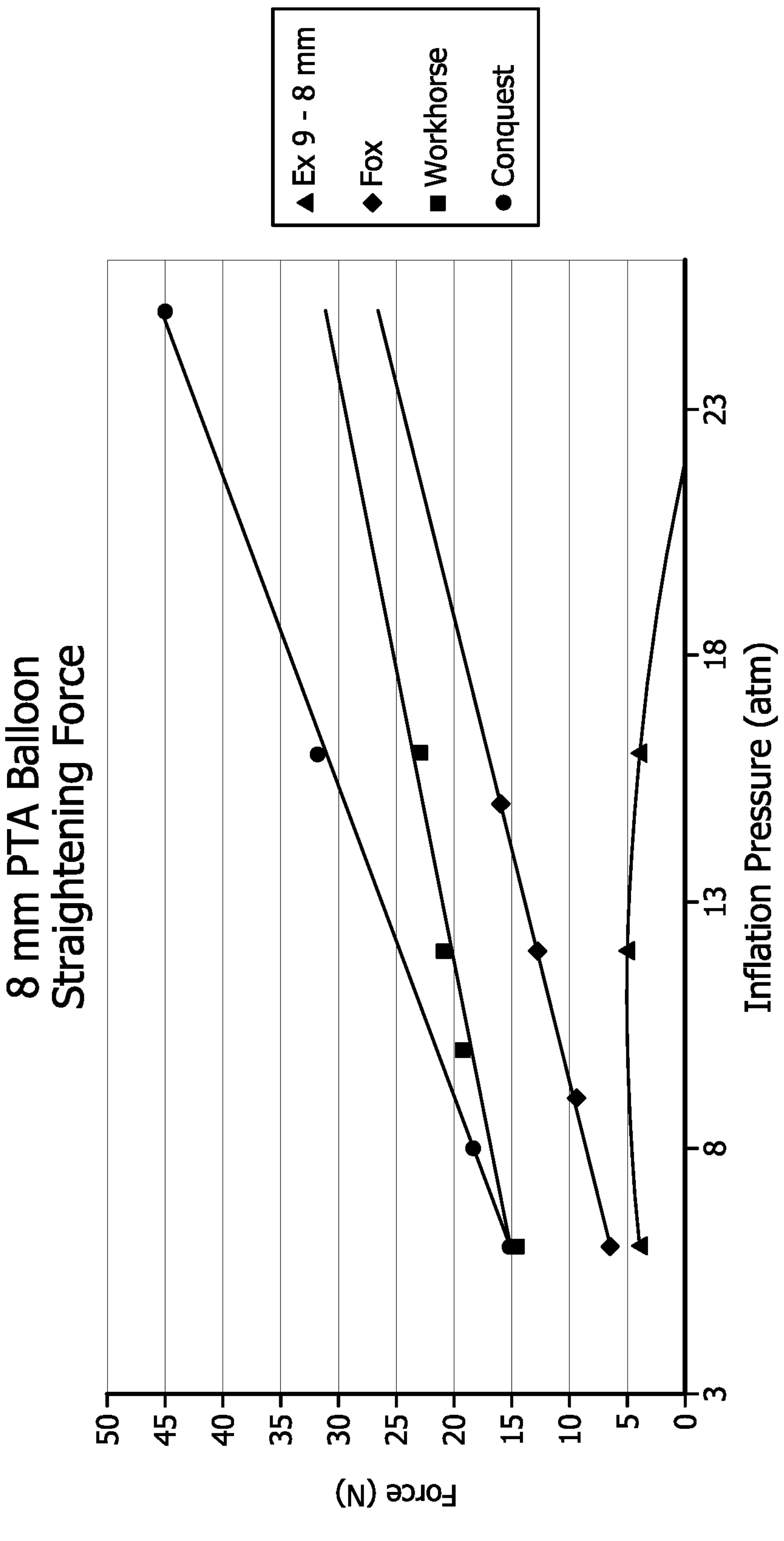
FIG. 13*c* is a plot showing the straightening force as a function of pressure of an 8 mm nominal diameter balloon made in accordance with the present disclosure compared to other 8 mm PTA balloons, namely, the Bard "Conquest" balloon; the Abbott "FoxCross" balloon; and the AngioDynamics "Workhorse" balloon as described in Example 11.
Figure 13D:
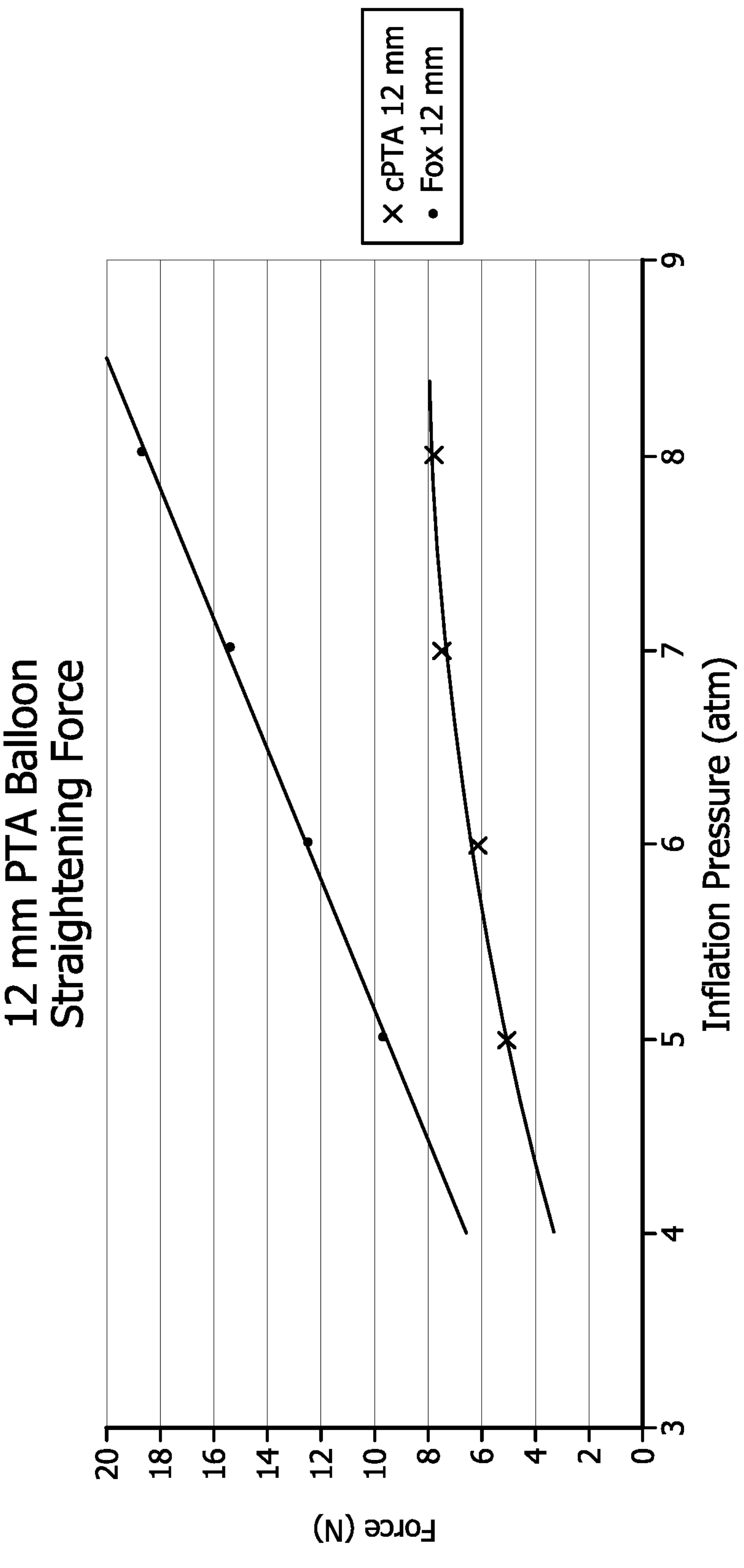
FIG. 13*d* is a plot showing the straightening force as a function of pressure of a 12 mm nominal diameter balloon made in accordance with the present disclosure compared to an Abbott "FoxCross" 12 mm balloon as described in Example 11.

Plots of the balloons tested are provided in FIGS. 13*a*-13*d*. As shown in each of these figures, the observed rate of change of the straightening force per unit of pressure is much lower for each of the conformable balloons (prepared in accordance with Examples 7-10) as compared to the Abbott FoxCross having the same diameter. As shown in FIG. 13*c*, in particular, the conformable balloon prepared in accordance with Example 9 demonstrated the lowest rate of change of the straightening force per unit of pressure as compared to other PTA balloons sold by Bard, Abbott, and Angiodynamics.

This example demonstrates that medical balloons—made in accordance with the present disclosure and having a nominal diameter between about 3 mm to about 8 mm and a nominal inflation pressure at or below 10 atm—exhibit less than a 13% increase in mean straightening force when inflated from a pressure of 10 atm to 14 atm while in a curved conformation requiring 16% total strain. In addition, such balloons exhibit a mean straightening force of less than 5 N when inflated up to a pressure of 17 atm while in a curved conformation requiring 16% total strain. Specifically, under such conditions, the 5 mm diameter balloon exhibited a mean straightening force of less than 4N, and the 8 mm diameter balloon exhibited less than 5N.

Similarly, medical balloons—made in accordance with the present disclosure and having a nominal diameter between about 9 mm to about 12 mm and a nominal pressure at or below 6 atm—exhibit less than a 3N increase in mean straightening force when inflated from a pressure of 5 atm to 8 atm while in a curved conformation requiring 16% total strain. In addition, such balloons exhibit a mean straightening force of less than 8 N when inflated up to a pressure of 8 atm while in a curved conformation requiring 16% total strain.

Moreover, it can be inferred from this example, that a medical balloon—made in accordance with the present disclosure and having a nominal diameter between about 13 mm to about 14 mm and a nominal inflation pressure at or below 6 atm—exhibits less than about 3.5N increase in mean straightening force when inflated from a pressure of 6 atm to 8 atm while in a curved conformation requiring approximately 16% total strain. In addition, such balloons can exhibit a mean straightening force of less than 11 N when inflated up to 8 atm while in a curved conformation requiring 16% total strain.

Figure 14A:
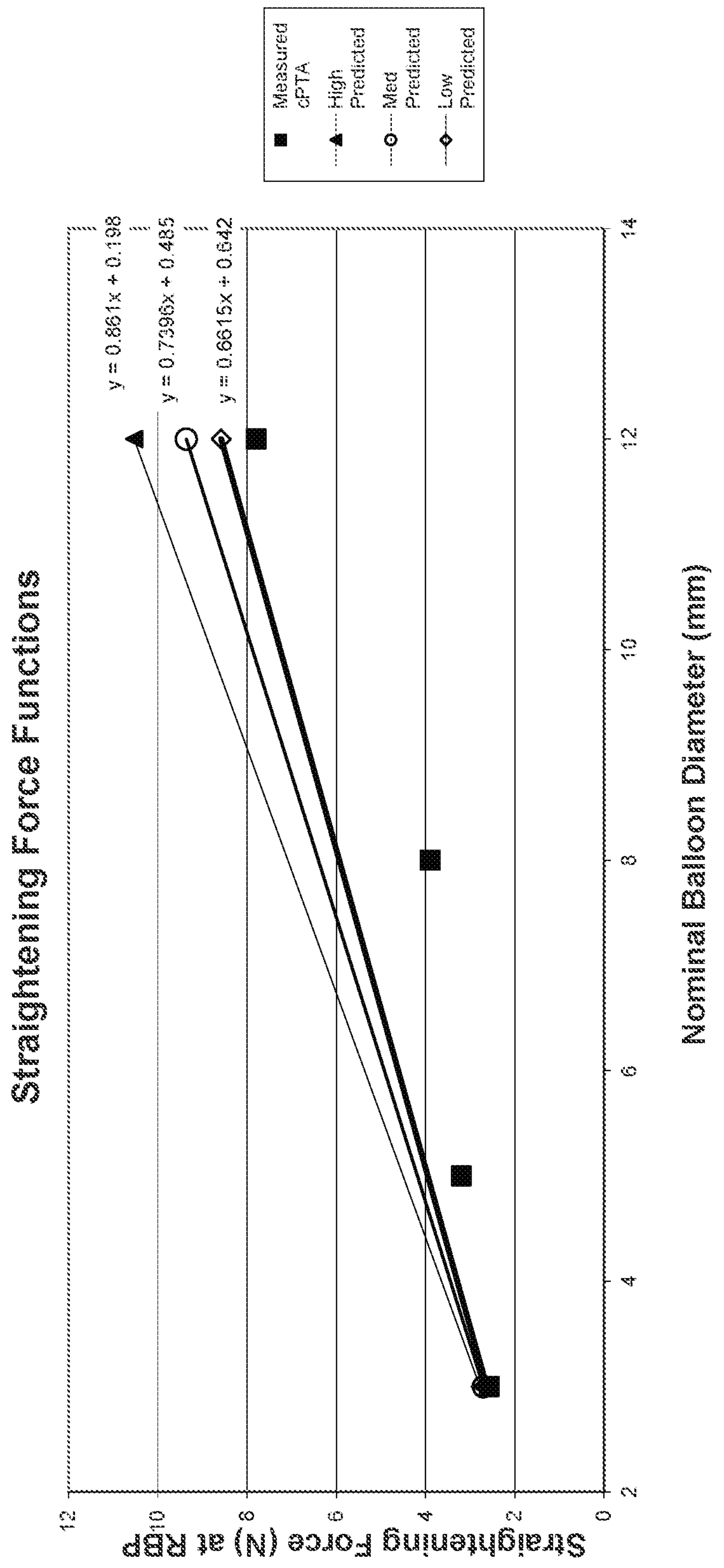
FIG. 14*a* is a graph plotting the straightening force at the rated burst pressure for a 3, 5, 8, and 12 mm conformable balloon and the threshold trend lines.
Figure 14B:
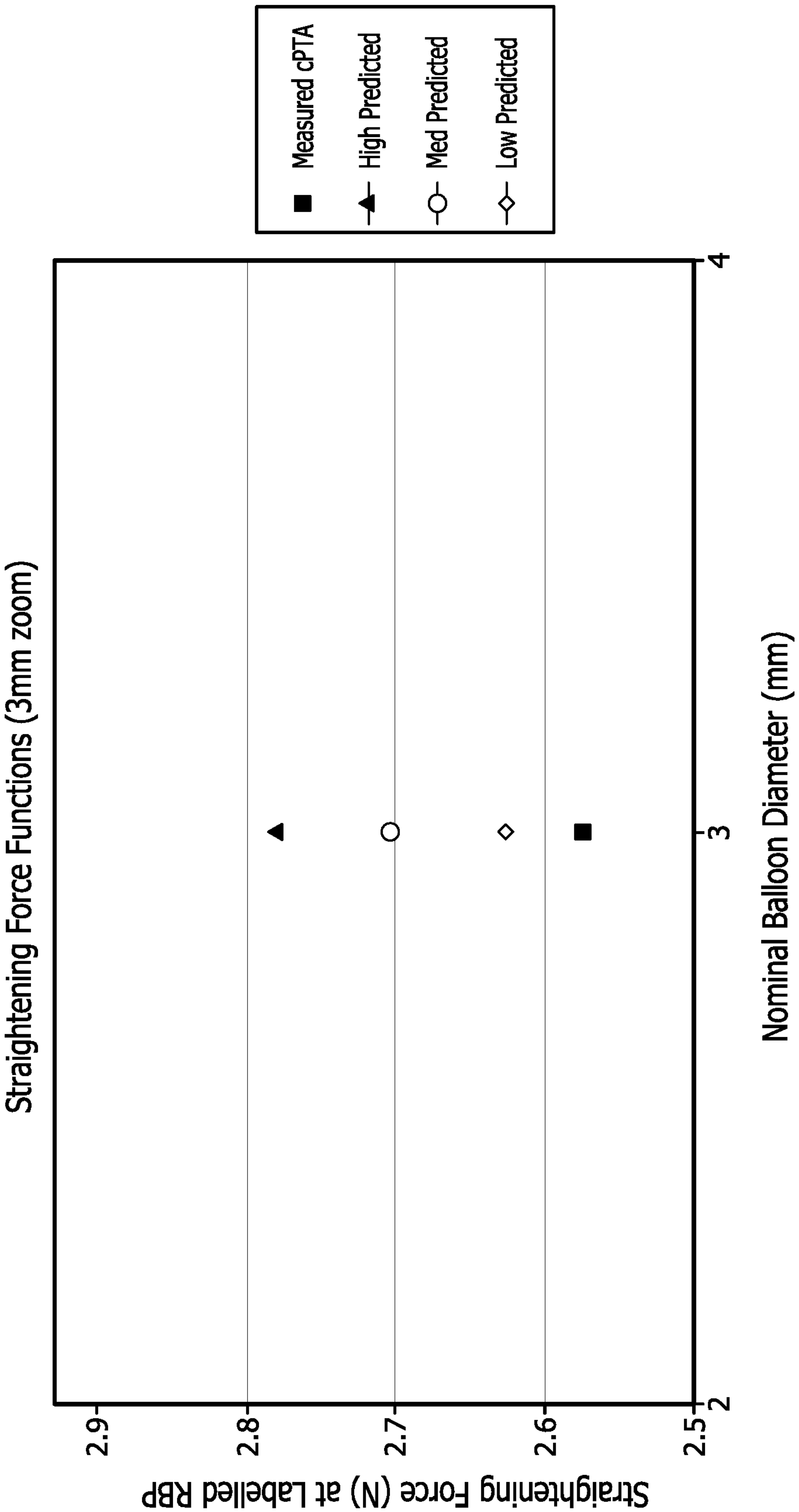
FIG. 14*b* shows the straightening force at the rated burst pressure for the 3 mm conformable balloon and the lower end point of the threshold trend lines.

FIG. 14*a* is a graph plotting the straightening force at the rated burst pressure for the 3, 5, 8, and 12 mm conformable balloon. Based on this data, predictive trend lines of a maximum straightening force at the rated burst pressure for balloons ranging from 3-12 mm are plotted. A conformable balloon of the present disclosure within about 3 to about 12 mm in diameter will have a straightening force at the rated burst pressure that can be less than 0.86(Diameter)+0.20; less than 0.74(Diameter)+0.49; or even less than 0.66(Diameter)+0.64. The trend line formulas are based on the following increases (see Table 2) to the observed 3 mm straightening force at rated (2.575 N) and the observed 12 mm straightening force at rated (7.8 N).

TABLE 2

| Trend line formula | % increase at 3 mm | % increase at 12 mm |
|---|---|---|
| 0.86(Diameter) + 0.20 | 8 | 35 |
| 0.74(Diameter) + 0.49 | 5 | 20 |
| 0.66(Diameter) + 0.64 | 2 | 10 |

Numerous characteristics and advantages have been set forth in the preceding description, including various alternatives together with details of the structure and function of the devices and/or methods. The disclosure is intended as illustrative only and as such is not intended to be exhaustive. For example, embodiments of the present disclosure are described in the context of medical applications but can also be useful in non-medical applications. It will be evident to those skilled in the art that various modifications may be made, especially in matters of structure, materials, elements, components, shape, size, and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

What is claimed is:

1. A method of making a medical balloon assembly including a balloon having an outer wall, the method comprising:
- wrapping an anisotropic, porous film about a mandrel at an angle of 75 degrees or more with respect to a longitudinal axis to form a tubular precursor; and
- overlying the tubular precursor over at least a portion of the outer wall of the balloon, the tubular precursor forming a template, wherein the template is formed of a wrapped, polymeric material that forms a structure having a plurality of apertures, and wherein the template has about the same longitudinal stiffness as the outer wall of the balloon.

2. The method of claim 1, further comprising forming the plurality of apertures in the template, wherein forming a plurality of apertures in the template further comprises at least one of cutting, stamping, laser cutting, perforating, and/or punching.

3. The method of claim 1, further comprising forming the plurality of apertures in the template, wherein forming a plurality of apertures in the template further comprises removing or otherwise weaking a material of the template to form an aperture.

4. The method of claim 2, further comprising inflating the balloon to an inflated configuration wherein a portion of the outer wall of the balloon protrudes through the apertures of the template.

5. The method of claim 4, wherein inflating the balloon to an inflated configuration is such that the balloon uniformly expands through the apertures of the template.

6. The method of claim 1, wherein wrapping the anisotropic, porous film about the mandrel further comprises selecting the mandrel to have a diameter less than a nominal diameter of the balloon such that a nominal diameter of the template is less than the nominal diameter of the balloon.

7. The method of claim 1, wherein wrapping the anisotropic, porous film about the mandrel is at an angle greater than 80 degrees with respect to a longitudinal axis.

8. The method of claim 1, further including applying an implantable device about an outer surface of the template.

9. The method of claim 1, wherein wrapping the anisotropic, porous film about the mandrel is at an angle of about 75 degrees to about 88 degrees with respect to a longitudinal axis.

10. The method of claim 1, wherein the template is formed to have a circumferential stiffness greater than that of the outer wall of the balloon.

11. The method of claim 1, further comprising coating at least a portion of the outer wall of the balloon with a therapeutic agent.

12. A method of making a medical balloon assembly including a balloon having an outer wall, the method comprising:
- forming an anisotropic, porous material with a wrap angle of 75 degrees or more with respect to a longitudinal axis of the anisotropic, porous material to form a template, wherein the template defines a structure having a plurality of apertures, and wherein the template has a circumferential stiffness greater than that of the outer wall of the balloon; and
- coupling the template to a portion of the outer wall of the balloon.

13. The method of claim 12, further comprising inflating the balloon to an inflated configuration wherein a portion of the outer wall of the balloon protrudes through the apertures of the template.

14. The method of claim 12, wherein inflating the balloon to an inflated configuration is such that the balloon uniformly expands through the apertures of the template.

15. The method of claim 12, further including applying an implantable device about an outer surface of the template.

16. The method of claim 12, further comprising coating at least a portion of the outer wall of the balloon with a therapeutic agent.

17. A method of making a medical assembly comprising:
- wrapping a polymeric material to form a template, the template defining a plurality of apertures through a thickness of the template;
- overlying the template over at least a portion of an outer surface of a compliant bladder; and
- attaching the outer surface of the compliant bladder to the inner surface of the template.

18. The method of claim 17, further including applying an implantable device about an outer surface of the template.

19. The method of claim 17, wherein overlaying the template includes maintaining portions of the compliant bladder uncovered by the template at positions of the compliant bladder that align with the plurality of apertures.

20. The method of claim 17, further comprising coating at least a portion of the outer wall of the balloon with a therapeutic agent.

* * * * *